(12) United States Patent
Pretz

(10) Patent No.: US 11,298,671 B2
(45) Date of Patent: Apr. 12, 2022

(54) BULK CATALYST WITHDRAWAL SYSTEM AND METHODS FOR THE USE THEREOF

(71) Applicant: Dow Global Technologies LLC, Midland, MI (US)

(72) Inventor: Matthew T. Pretz, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 70 days.

(21) Appl. No.: 16/609,905

(22) PCT Filed: May 3, 2018

(86) PCT No.: PCT/US2018/030761
§ 371 (c)(1),
(2) Date: Oct. 31, 2019

(87) PCT Pub. No.: WO2018/204562
PCT Pub. Date: Nov. 8, 2018

(65) Prior Publication Data
US 2020/0055015 A1    Feb. 20, 2020

Related U.S. Application Data

(60) Provisional application No. 62/502,094, filed on May 5, 2017.

(51) Int. Cl.
*B01J 8/26* (2006.01)
*B01J 8/00* (2006.01)
(Continued)

(52) U.S. Cl.
CPC .................. *B01J 8/26* (2013.01); *B01J 8/003* (2013.01); *B01J 8/005* (2013.01); *B01J 8/1827* (2013.01);
(Continued)

(58) Field of Classification Search
CPC . B01J 8/0025; B01J 8/003; B01J 8/005; B01J 8/0055; B01J 8/1827; B01J 8/1863;
(Continued)

(56) References Cited

U.S. PATENT DOCUMENTS 4,547,616 A   10/1985  Avidan et al.
4,579,716 A    4/1986  Krambeck et al.
(Continued)

FOREIGN PATENT DOCUMENTS

WO   2005026294 A1   3/2005
WO   2005077867 A2   8/2005
(Continued)

OTHER PUBLICATIONS

Bolebruch ("Key factors in selecting refractories." Hydrocarbon processing (International ed.) 86(3) 2007, pp. 65-66) (Year: 2007).*
(Continued)

*Primary Examiner* — Philip Y Louie
*Assistant Examiner* — Jason Y Chong
(74) *Attorney, Agent, or Firm* — Dinsmore & Shohl LLP

(57) ABSTRACT

A method for processing a chemical stream includes contacting a feed stream with a catalyst in a reactor portion of a reactor system causing a reaction which forms a product stream. The method includes separating the product stream from the catalyst, passing the catalyst to a catalyst processing portion of the reactor system, processing the catalyst in the catalyst processing portion, and passing a portion of the catalyst from the catalyst processing portion of the reactor system into a catalyst withdrawal system that includes a catalyst withdrawal vessel and a transfer line coupling the catalyst withdrawal vessel to the catalyst processing portion. Each of the catalyst withdrawal vessel and the transfer line include an outer metallic shell and an inner refractory lining. The method further includes cooling the catalyst in the
(Continued)

catalyst withdrawal vessel from greater than or equal to 680° C. to less than or equal to 350° C.

14 Claims, 6 Drawing Sheets

(51) Int. Cl.
  *B01J 8/18* (2006.01)
  *B01J 38/30* (2006.01)
  *C07C 5/333* (2006.01)
(52) U.S. Cl.
  CPC .......... *B01J 8/1863* (2013.01); *B01J 38/30* (2013.01); *C07C 5/333* (2013.01); *B01J 2208/00769* (2013.01); *B01J 2219/00247* (2013.01)
(58) Field of Classification Search
  CPC ..... B01J 8/26; B01J 8/388; B01J 38/30; B01J 2208/00008; B01J 2208/00017; B01J 2208/00672; B01J 2208/00769; B01J 2208/00955; C10G 11/18
  See application file for complete search history.

(56) References Cited

U.S. PATENT DOCUMENTS

| | | | |
|---|---|---|---|
| 5,190,650 A | 3/1993 | Tammera et al. | |
| 5,275,641 A | 1/1994 | Tammera et al. | |
| 5,343,939 A * | 9/1994 | Cetinkaya | B01J 38/32 165/104.16 |
| 6,362,385 B1 * | 3/2002 | Iezzi | B01J 23/26 585/654 |
| 7,038,098 B2 * | 5/2006 | Walsdorff | C07C 5/327 585/319 |
| 7,090,081 B2 | 8/2006 | Vaughn et al. | |
| 7,431,894 B2 | 10/2008 | Evans | |
| 8,092,756 B2 | 1/2012 | Evans et al. | |
| 8,146,414 B2 | 4/2012 | Evans et al. | |
| 8,236,247 B2 | 8/2012 | Evans et al. | |
| 8,669,406 B2 | 3/2014 | Pretz et al. | |
| 2010/0154891 A1 | 6/2010 | Evans et al. | |
| 2016/0114316 A1 | 4/2016 | Palmas et al. | |

FOREIGN PATENT DOCUMENTS

| | | |
|---|---|---|
| WO | 2007011808 A2 | 1/2007 |
| WO | 2013126210 A1 | 8/2013 |

OTHER PUBLICATIONS

Resco ("Product Data" https://www.rescoproducts.com/media/documents/data_sheets/PDS/Vibrocast%20FS-6.pdf, updated Apr. 3, 2017). (Year: 2017).*
International Search Report and Written Opinion pertaining to PCT/US2018/030761, dated Sep. 7, 2018.
ASTM International, "Standard Test Method for Quantitatively Measuring the Effect of thermal Shock and Thermal Cycling on Refractories", (2003).
Fisher-Klosterman, Inc., "Product Bulletin: EX Series Aerodynamic Particle Classifier," (2000).
Kingery et al., "Introduction to Ceramics", Second Edition, Wiley-Interscience (1960), p. 824.
Mt. Savage Specialty Refractories Company, "Product Data Sheet: ULTRA-TEK FS—Fused Silica, Low Cement, Self Flow, Pump Mix, Shotcrete Mix," available at http://www.mtsavage.com/LinkClick.aspx?fileticket=YSP5oSpDcos%3d&tabid=120&mid=587 (last accessed Oct. 20, 2019).
Mt. Savage Specialty Refractories Company, Product Data Sheet: ULTRA-TEK FS Al—Low Cement Fused Silica, Aluminum Resistant Castable, available at http://www.mtsavage.com/LinkClick.aspx?fileticket=o%2fVismZDvNk%3d&tabid=120&mid=587 (last accessed Oct. 20, 2019).
Resco Products, Inc, "Product Data Sheet: EZ Cubed 270," (2016), available at http://www.rescoproducts.com/docs/PDS/EZ%20Cubed%20FS-6PC%20PDS.pdf (last accessed Oct. 20, 2019).
Resco Products (UK) Ltd., "Product Data Sheet: Quickturn FS-6G," (2013), available at http://www.rescoproducts.com/docs/PDS/Quikturn%20FS-PC%20PDS.pdf (last accessed Oct. 20, 2019).
Resco Products (UK) Ltd., "Product Data Sheet: Sureflow FS-6LC," (2013), available at http://www.rescoproducts.com/docs/PDS/Sureflow%20FS%206LC%20PDS.pdf (last accessed Oct. 20, 2019).
Spar, Inc. Refractory Specialists, "Product Data Sheet: SPARSHOT FS-P," available at http://www.sparref.com/uploadedFiles/File/Products_Document_1214338937.pdf (last accessed Oct. 20, 2019).
Spar, Inc. Refractory Specialists, "Product Data Sheet: SPARCON FS60 P," (2003) available at http://www.sparref.com/uploadedFiles/File/Products_Document_1214316643.pdf (last accessed Oct. 20, 2019).
Thermal Ceramics, "Product Data Sheet: Tri-Mor Fused Silica Castable," available at https://www.cumi-murugappa.com/refractories/datasheet/pro-trimor-fused-silica-castable.pdf (last accessed Oct. 20, 2019).
Grimshaw, Rex W., "The Chemistry and Physics of Clays and Allied Ceramic Materials", Fourth Edition, Wiley-Interscience (1971), p. 797.

* cited by examiner

BULK CATALYST WITHDRAWAL SYSTEM AND METHODS FOR THE USE THEREOF

CROSS REFERENCE TO RELATED APPLICATION

This application is a National Stage Entry under 35 U.S.C. § 371 of International Patent Application No. PCT/US2018/030761 filed May 3, 2018, which claims the benefit of U.S. Provisional Patent Application Ser. No. 62/502,094 filed May 5, 2017, both of which are hereby incorporated by reference in their entirety.

BACKGROUND

Field

The present disclosure generally relates to chemical processing systems and, more specifically, to catalyst withdrawal systems for chemical processing systems.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene. Light olefins may be produced by different reaction processes depending on the given chemical feed stream, which may be a product stream from a crude oil refining operation. Many light olefins may be produced through catalytic processes, such as catalytic hydrogenation for example, in which the feed stream is contacted with a fluidized catalyst that facilitates conversion of the feed stream into the light olefins. Over time, the catalyst may become deactivated and must be removed from the reaction process and replaced.

BRIEF SUMMARY

There is a continued need for improved systems and methods for removing catalyst from reactor systems, such as reactor systems for processing chemical streams to produce light olefins or other chemical products. Many reactor systems for processing chemical streams to produce light olefins and other chemicals utilize hot catalyst, such as those that have been heated to temperatures greater than 350° C. The catalyst may be circulated through reaction systems, such as through a reaction portion (where chemical products are made) and through a regeneration portion (where the catalyst is regenerated such as by removal of coke or by heating). Over time, these catalysts may become permanently deactivated through contamination or loss/deterioration of a catalytically active material on the catalyst. In additional embodiments, these deactivated catalysts may be reactivated through processes only available outside of the reactor system. As such, the deactivated catalyst may need to be removed from the reactor system either continuously, semi-continuously, or intermittently with batch withdrawal.

However, removal of hot catalyst from reactor systems may result in damage to and/or rapid deterioration of process equipment, such as transfer piping, catalyst bins, catalyst vessels, valves, or other equipment used to remove the hot catalyst from the reactor system. For example, removal of hot catalyst having temperatures in excess of 350° C. may cause deformation of equipment made from carbon steel, stainless steel, or other customary handling and storage materials.

To mitigate damage to equipment caused by withdrawing hot catalyst from the reactor system, refractory materials may be used as internal linings of tanks and piping. However, refractory materials may still experience substantial cracking and deterioration when subjected to thermal cycling during batch withdrawal of the catalysts. As used herein, "thermal cycling" refers to cyclically raising and lowering the temperature of a structure. For example, customarily employed refractory materials may crack when exposed to thermal cycling between temperatures equal to or less than 350° C. and temperatures in excess of 680° C. (i.e., the temperature of the withdrawn catalyst), which may cause failure of the metallic portions of the withdrawal equipment.

According to one or more embodiments, the catalyst withdrawal systems and methods disclosed herein solve these problems by providing a withdrawal system that may include a withdrawal vessel with an outer metallic shell and an inner refractory lining made from a thermal shock resistant refractory material that may withstand the temperatures of the hot catalyst as well as thermal cycling of the withdrawal vessel. The withdrawal systems and methods disclosed herein may reduce damage to the withdrawal system and, in some embodiments, may enable batch and continuous withdrawal of catalyst from the reactor system and cooling of the withdrawn catalyst without deforming the outer metallic shell of the vessel.

According to one embodiment, a method for processing a chemical stream may include contacting a feed stream with a catalyst in a reactor portion of a reactor system, wherein the contacting of the feed stream with the catalyst may cause a reaction which forms a product stream. The reactor system may comprise the reactor portion and a catalyst processing portion. The method may further include separating at least a portion of the product stream from the catalyst, passing the catalyst to the catalyst processing portion of the reactor system, processing the catalyst in the catalyst processing portion of the reactor system, and passing at least a portion of the catalyst from the catalyst processing portion of the reactor system into a catalyst withdrawal system. The catalyst withdrawal system may include a catalyst withdrawal vessel and a transfer line coupling the catalyst withdrawal vessel to the catalyst processing portion. Each of the catalyst withdrawal vessel and the transfer line may have an outer metallic shell and an inner refractory lining. The method may further include cooling the catalyst in the catalyst withdrawal vessel from greater than or equal to 680° C. to less than or equal to 350° C.

In another embodiment, a method for processing a chemical stream may include contacting a feed stream with a catalyst in a reactor portion of a reactor system, wherein contacting the feed stream with the catalyst may cause a reaction which forms a product stream. The reactor system may include the reactor portion and a catalyst processing portion. The method may further include separating at least a portion of the product stream from the catalyst, passing the catalyst to a catalyst processing portion of the reactor system, and processing the catalyst in the catalyst processing portion of the reactor system. Processing the catalyst may include raising the temperature of the catalyst, removing coke deposits from the catalyst, or both in a combustor of the catalyst processing portion of the reactor system. The method may further include passing at least a portion of the catalyst from the catalyst processing portion of the reactor system into a catalyst withdrawal system that may include a catalyst withdrawal vessel and a transfer line coupling the catalyst withdrawal vessel to the catalyst processing portion. Each of the catalyst withdrawal vessel and the transfer line may include an outer metallic shell and an inner refractory lining. The inner refractory lining of the catalyst withdrawal vessel may comprise a thermal shock resistant refractory material comprising at least one of fused silica, vitreous silica, cordierite, or combinations of these. The catalyst withdrawn from the catalyst processing portion may have a temperature of at least 680° C.

In still other embodiments, a system for processing a catalyst may include a combustor fluidly coupled to a reactor portion of a reactor system, the combustor configured to receive catalyst from the reactor portion of the reactor system and combust a fuel gas, coke deposits formed on the catalyst in the reactor portion of the reactor system, or both. The system may further include a riser downstream of the combustor and a catalyst separation section downstream of the riser. The catalyst separation section may comprise a catalyst outlet fluidly coupled to an inlet of the reactor portion of the reactor system configured for returning combusted catalyst back to the reactor portion. The system may further include a catalyst withdrawal system fluidly coupled to the catalyst separation section. The catalyst withdrawal system may include a catalyst withdrawal vessel and a transfer line coupling the catalyst withdrawal vessel to the catalyst separation section. Each of the catalyst withdrawal vessel and the transfer conduit may comprise an outer metallic shell and an inner refractory lining. The inner refractory lining of the catalyst withdrawal vessel may include a thermal shock resistant refractory material.

It is to be understood that both the foregoing brief summary and the following detailed description present embodiments of the technology, and are intended to provide an overview or framework for understanding the nature and character of the technology as it is claimed. The accompanying drawings are included to provide a further understanding of the technology, and are incorporated into and constitute a part of this specification. The drawings illustrate various embodiments and, together with the description, serve to explain the principles and operations of the technology. Additionally, the drawings and descriptions are meant to be merely illustrative, and are not intended to limit the scope of the claims in any manner.

Additional features and advantages of the technology disclosed herein will be set forth in the detailed description which follows, and in part will be readily apparent to those skilled in the art from that description or recognized by practicing the technology as described herein, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
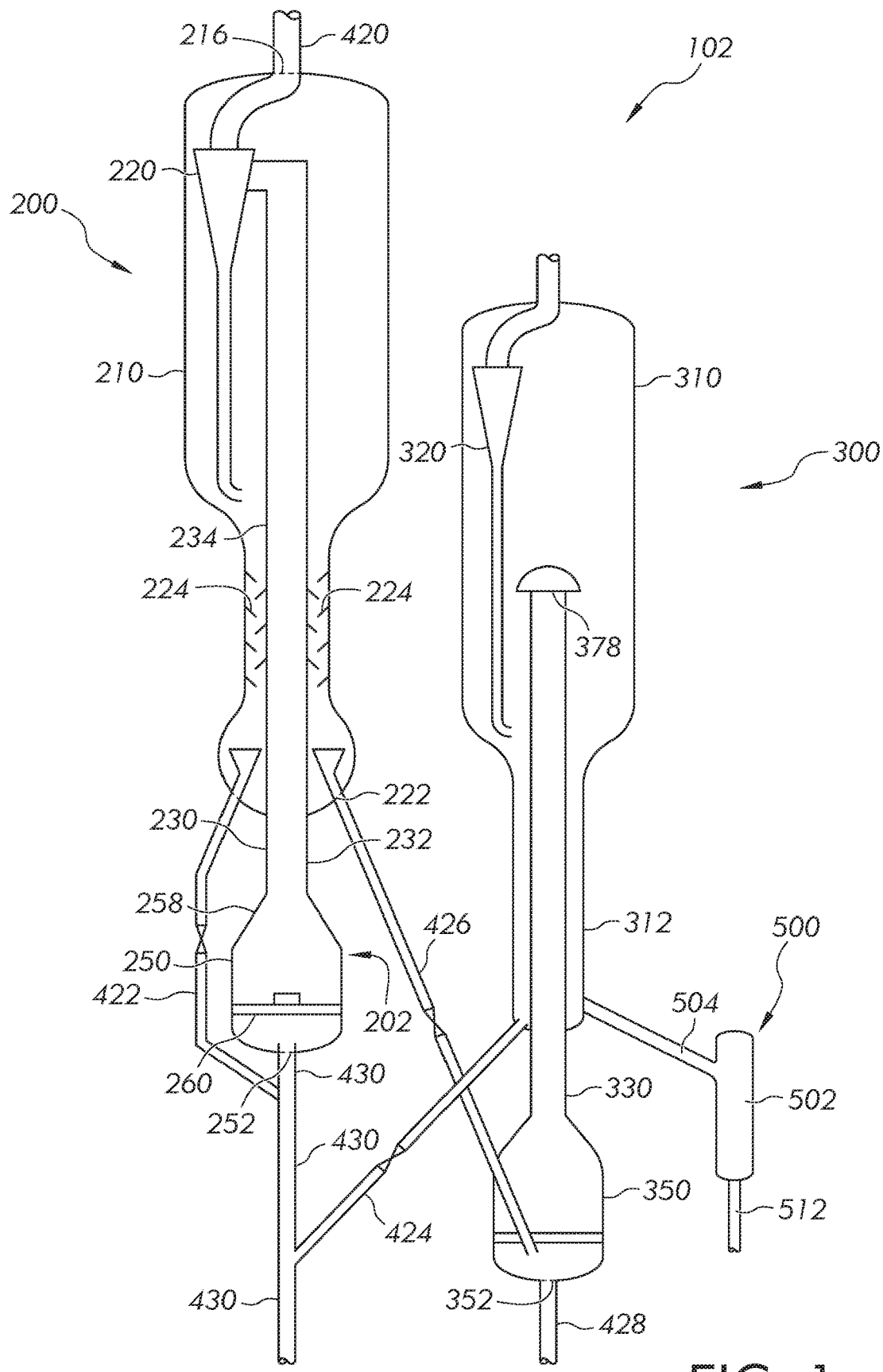
FIG. 1 schematically depicts a reactor system, according to one or more embodiments described herein.

It should be understood that the drawings are schematic in nature, and do not include some components of a reactor system commonly employed in the art, such as, without limitation, temperature transmitters, pressure transmitters, flow meters, pumps, valves, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

The catalyst withdrawal systems disclosed herein may include a catalyst withdrawal vessel closely coupled to the reactor system, such as closely coupled to the catalyst processing portion of the reactor system. The withdrawal vessel may have an inner refractory lining that may be a thermal shock resistant refractory material that may resist cracking and rapid deterioration caused by thermal conditions present when contacted by hot catalyst. In some embodiments, the catalyst withdrawal system with the inner refractory lining may provide improved service life compared to existing catalyst removal devices. The catalyst withdrawal systems disclosed herein may also provide flexibility to withdraw catalyst on a continuous or batch basis to adapt the catalyst withdrawal system to different reactor system configurations that may be used to convert different feed streams into light olefins or other products. In additional embodiments, the catalyst withdrawal systems disclosed herein may be advantageous for chemical processing systems in which the rate of catalyst deactivation in the reaction system is reduced.

As previously discussed, the catalyst withdrawal systems disclosed herein may be utilized to withdraw/remove catalyst from reactor systems for processing chemical streams. In non-limiting examples, the reactor systems may be utilized to produce light olefins from hydrocarbon feed streams. Light olefins may be produced from a variety of feed streams by utilizing different catalysts and reaction mechanisms. For example, light olefins may be produced by at least dehydrogenation reactions, cracking reactions, dehydration reactions, and methanol-to-olefin reactions. These reaction types may utilize different feed streams which are subsequently reacted to form the light olefins. While the systems and methods for withdrawing catalyst are described herein the in the context of hydrocarbon processing to form light olefins, it should be understood that it is contemplated that the catalyst withdrawal systems and methods described herein may be utilized for withdrawing any solid material, such as any particulate catalyst, from a reactor system. As such, the presently described catalyst withdrawal systems and methods should not be limited only to embodiments for withdrawing catalyst from a hydrocarbon conversion system designed to produce light olefins, such as that depicted in FIG. 1.

The reactor systems and methods for processing the chemical streams will now be discussed in detail. The chemical stream that is processed may be referred to as a feed stream, which is processed by a reaction to form a product stream. The feed stream may comprise a composition, and depending upon that feed stream composition, an appropriate catalyst may be utilized to convert the contents of the feed stream into a product stream that includes light olefins or other chemical products. For example, a feed stream may comprise at least one of propane, butane, ethane, or ethylbenzene, and the reaction system may be a dehydrogenation system in which the feed stream may be converted to light olefins through dehydrogenation in the presence of a dehydrogenation catalyst, such as a catalyst comprising platinum, palladium, and/or gallium. Other catalysts and reaction mechanisms may be utilized to form light olefins from a hydrocarbon feed stream. Further discussion on appropriate catalysts for use with various feed streams is provided subsequently in this disclosure.

Now referring to FIG. 1, an example reactor system 102 is schematically depicted. However, it should be understood that the catalyst withdrawal systems 500 and withdrawal methods described herein may be suitable for use with other reactor system configurations, including those that do not include regeneration by cyclical catalyst movement as described herein. The reactor system 102 generally comprises multiple system components, such as a reactor portion 200, a catalyst processing portion 300, and a catalyst withdrawal system 500. As used herein in the context of FIG. 1, the reactor portion 200 generally refers to the portion of a reactor system 102 in which the major process reaction takes place. For example, the reactor system 102 may be a dehydrogenation system in which the feed stream is dehydrogenated in the presence of the dehydrogenation catalyst in the reactor portion 200 of the reactor system 102.

The reactor portion 200 comprises a reactor 202 which may include a downstream reactor section 230 and an upstream reactor section 250. According to one or more embodiments, as depicted in FIG. 1, the reactor portion 200 may additionally include a catalyst separation section 210 which serves to separate the catalyst from the chemical products formed in the reactor 202. Also, as used herein, the catalyst processing portion 300 generally refers to the portion of a reactor system 102 in which the catalyst is in some way processed, such as by combustion. The catalyst processing portion 300 may comprise a combustor 350 and a riser 330, and may optionally comprise a catalyst separation section 310. In some embodiments, the catalyst may be regenerated by burning off contaminants like coke in the catalyst processing portion 300. In additional embodiments, the catalyst may be heated in the catalyst processing portion 300. A supplemental fuel may be utilized to heat the catalyst in the catalyst processing portion 300 if coke or another combustible material is not formed on the catalyst, or an amount of coke formed on the catalyst is not sufficient to burn off to heat the catalyst to a desired temperature. In one or more embodiments, the catalyst separation section 210 may be in fluid communication with the combustor 350 (e.g., via standpipe 426) and the catalyst separation section 310 may be in fluid communication with the upstream reactor section 250 (e.g., via standpipe 424 and transport riser 430). The catalyst withdrawal system 500 may comprise a catalyst withdrawal vessel 502 and a transfer line 504 coupling the catalyst withdrawal vessel 502 to the catalyst processing portion 300.

As described with respect to FIG. 1, the feed stream may enter the transport riser 430, and the product stream may exit the reactor system 102 via pipe 420. According to one or more embodiments, the reactor system 102 may be operated by feeding a chemical feed (e.g., in a feed stream) and a fluidized catalyst into the upstream reactor section 250. The chemical feed contacts the catalyst in the upstream reactor section 250, and each flow upwardly into and through the downstream reactor section 230 to produce a chemical product. The chemical product and the catalyst may be passed out of the downstream reactor section 230 to a separation device 220 in the catalyst separation section 210. The catalyst is separated from the chemical product in the separation device 220. The chemical product is transported out of the catalyst separation section 210. The separated catalyst is passed from the catalyst separation section 210 to the combustor 350. In the combustor 350, the catalyst may be processed by, for example, combustion. For example, and without limitation, the catalyst may be de-coked and/or supplemental fuel may be combusted to heat the catalyst. The catalyst is then passed out of the combustor 350 and through the riser 330 to a riser termination separator 378, where the gas and solid components from the riser 330 are at least partially separated. The vapor and remaining solids are transported to a secondary separation device 320 in the catalyst separation section 310 where the remaining catalyst is separated from the gases from the catalyst processing (e.g., gases emitted by combustion of spent catalyst or supplemental fuel). The separated catalyst is then passed from the catalyst separation section 310 to the upstream reactor section 250 via standpipe 424 and transport riser 430, where it is further utilized in a catalytic reaction. Thus, the catalyst, in operation, may cycle between the reactor portion 200 and the catalyst processing portion 300. In general, the processed chemical streams, including the feed streams and product streams may be gaseous, and the catalyst may be fluidized particulate solid.

According to one or more embodiments described herein, the reactor portion 200 may comprise an upstream reactor section 250, a transition section 258, and a downstream reactor section 230, such as a riser. The transition section 258 may connect the upstream reactor section 250 with the downstream reactor section 230. According to one or more embodiments, the upstream reactor section 250 and the downstream reactor section 230 may each have a substantially constant cross-section area, while the transition section 258 may be tapered and does not have a constant cross-sectional area. As described herein, unless otherwise explicitly stated, the "cross-sectional area" refers to the area of the cross section of a portion of the reactor part in a plane substantially orthogonal to the direction of general flow of reactants and/or products. For example, in FIG. 1, the cross sectional area of the upstream reactor section 250, the transition section 258, and the downstream reactor section 230 is in the direction of a plane defined by the horizontal direction and the direction into the page (orthogonal to the direction of fluid motion, i.e., vertically upward in FIG. 1).

As depicted in FIG. 1, the upstream reactor section 250 may be positioned below the downstream reactor section 230. Such a configuration may be referred to as an upflow configuration in the reactor 202. The reactor 202 may also be a downflow reactor in which the upstream reactor section 250 may be position above the downstream reactor section 230. Other reactor configurations are also contemplated for the reactor portion 200 of the reactor system 102.

As described herein, the upstream reactor section 250 may include a vessel, drum, barrel, vat, or other container suitable for a given chemical reaction. In one or more embodiments, the upstream reactor section 250 may be generally cylindrical in shape (i.e., having a substantially circular cross-sectional shape), or may alternately be non-cylindrically shaped, such as prism shaped with cross-sectional shapes of triangles, rectangles, pentagons, hexagons, octagons, ovals, or other polygons or curved closed shapes, or combinations thereof. The upstream reactor section 250, as used throughout this disclosure, may generally include a metallic frame, and may additionally include refractory linings or other materials utilized to protect the metallic frame and/or control process conditions. As depicted in FIG. 1, the upstream reactor section 250 may include a lower reactor portion catalyst inlet port 252 defining the connection of transport riser 430 to the upstream reactor section 250.

The upstream reactor section 250 may be connected to a transport riser 430 which, in operation, may provide processed catalyst and/or reactant chemicals in a feed stream to the reactor portion 200. The processed catalyst and/or reactant chemicals may be mixed with a distributor 260 housed in the upstream reactor section 250. The catalyst entering the upstream reactor section 250 via transport riser 430 may be passed through standpipe 424 to a transport riser 430, thus arriving from the catalyst processing portion 300. In some embodiments, catalyst may come directly from the catalyst separation section 210 via standpipe 422 and into a transport riser 430, where it enters the upstream reactor section 250. The catalyst can also be fed via 422 directly to the upstream reactor section 250. This catalyst may be slightly deactivated, but may still, in some embodiments, be suitable for reaction in the upstream reactor section 250. As used herein, "deactivated" may refer to a catalyst which is contaminated with a substance such as coke, or is cooler in temperature than desired. Regeneration may remove the contaminant such as coke, raise the temperature of the catalyst, or both.

Still referring to FIG. 1, the reactor portion 200 may comprise a downstream reactor section 230 which acts to transport reactants, products, and/or catalyst from the upstream reactor section 250 to the catalyst separation section 210. In one or more embodiments, the downstream reactor section 230 may be generally cylindrical in shape (i.e., having a substantially circular cross-sectional shape), or may alternately be non-cylindrically shaped, such as prism shaped with cross-sectional shape of triangles, rectangles, pentagons, hexagons, octagons, ovals, or other polygons or curved closed shapes, or combinations thereof. The downstream reactor section 230, as used throughout this disclosure, may generally include a metallic frame, and may additionally include refractory linings or other materials utilized to protect the metallic frame and/or control process conditions.

According to some embodiments, the downstream reactor section 230 may include an external riser section 232 and an internal riser section 234. As used herein, an "external riser section" refers to the portion of the riser that is outside of the catalyst separation section 210, and an "internal riser section" refers to the portion of the riser that is within the catalyst separation section 210. For example, in the embodiment depicted in FIG. 1, the internal riser section 234 of the reactor portion 200 may be positioned within the catalyst separation section 210, while the external riser section 232 is positioned outside of the catalyst separation section 210.

As depicted in FIG. 1, the upstream reactor section 250 may be connected to the downstream reactor section 230 via the transition section 258. The upstream reactor section 250 may generally comprise a greater cross-sectional area than the downstream reactor section 230. The transition section 258 may be tapered from the size of the cross-section of the upstream reactor section 250 to the size of the cross-section of the downstream reactor section 230 such that the transition section 258 projects inwardly from the upstream reactor section 250 to the downstream reactor section 230.

In some embodiments, such as those in which the upstream reactor section 250 and the downstream reactor section 230 have similar cross-sectional shapes, the transition section 258 may be shaped as a frustum. For example, for an embodiment of a reactor portion 200 comprising a cylindrical upstream reactor section 250 and cylindrical downstream reactor section 230, the transition section 258 may be shaped as a conical frustum. However, it should be understood that a wide variety of upstream reactor section 250 shapes are contemplated herein which connect various shapes and sizes of upstream reactor section 250 and downstream reactor section 230.

In one or more embodiments, the upstream reactor section 250 may have an average cross-sectional area that is at least 150% of the average cross-sectional area of the downstream reactor section 230. As described herein, an "average cross-sectional area" refers to the mean of the cross-sectional areas for a given system component or section such as the upstream reactor section 250 or the downstream reactor section 230. If the system component or section has a substantially constant cross-sectional area, such as the cylindrical shapes of the depicted upstream reactor section 250 or the downstream reactor section 230, then the cross-sectional area at any point is about equal to the average cross-sectional area.

According to one or more embodiments, the upstream reactor section 250 may have an average cross-sectional area that is at least 160%, at least 170%, at least 180%, at least 190%, at least 200%, at least 250%, at least 300%, at least 400% or even at least 500% of the average cross-sectional area of the downstream reactor section 230.

In one or more embodiments, based on the shape, size, and other processing conditions such as temperature and pressure in the upstream reactor section 250 and the downstream reactor section 230, the upstream reactor section 250 may operate in a manner that is or approaches isothermal, such as in a fast fluidized, turbulent, or bubbling bed upflow reactor, while the downstream reactor section 230 may operate in more of a plug flow manner, such as in a riser reactor. For example, the reactor 202 of FIG. 1 may comprise an upstream reactor section 250 operating as a fast fluidized, turbulent, or bubbling bed reactor and a downstream reactor section 230 operating as a dilute phase riser reactor, with the result that the average catalyst and gas flow moves concurrently upward. As the term is used herein, "average flow" refers to the net flow, i.e., the total upward flow minus the retrograde or reverse flow, as is typical of the behavior of fluidized particles in general. As described herein, a "fast fluidized" reactor may refer to a reactor utilizing a fluidization regime wherein the superficial velocity of the gas phase is greater than the choking velocity and may be semi-dense in operation. As described herein, a "turbulent" reactor may refer to a fluidization regime wherein the superficial velocity of less than the choking velocity and is more dense than the fast fluidized regime. As described herein, a "bubbling bed" reactor may refer to a fluidization regime wherein well defined bubbles in a highly dense bed are present in two distinct phases. The "choking velocity" refers to the minimum velocity required to maintain solids in the dilute-phase mode in a vertical conveying line. As described herein, a "dilute phase riser" may refer to a riser reactor operating at transport velocity, wherein the gas and catalyst have about the same velocity in a dilute phase.

In one or more embodiments, the pressure in the reactor 202 may range from 6.0 to 44.7 pounds per square inch absolute (psia, from about 41.4 kilopascals, kPa, to about 308.2 kPa), but in some embodiments, a narrower selected range, such as from 15.0 psia to 35.0 psia, (from about 103.4 kPa to about 241.3 kPa), may be be employed. For example, the pressure may be from 15.0 psia to 30.0 psia (from about 103.4 kPa to about 206.8 kPa), from 17.0 psia to 28.0 psia (from about 117.2 kPa to about 193.1 kPa), or from 19.0 psia to 25.0 psia (from about 131.0 kPa to about 172.4 kPa). Unit conversions from standard (non-SI) to metric (SI) expressions herein include "about" to indicate rounding that may be present in the metric (SI) expressions as a result of conversions.

In additional embodiments, the weight hourly space velocity (WHSV) for the disclosed process may range from 0.1 pound (lb) to 100 lb of chemical feed per hour (h) per lb of catalyst in the reactor (lb feed/h/lb catalyst). For example, where the reactor 202 comprises an upstream reactor section 250 that operates as a fast fluidized, turbulent, or bubbling bed reactor and a downstream reactor section 230 that operates as a dilute phase riser reactor, the superficial gas velocity may range therein from 2 ft/s (about 0.61 m/s) to 10 ft/s (about 3.05 m/s) in the upstream reactor section 250, and from 30 ft/s (about 9.14 m/s) to 70 ft/s (about 21.31 m/s) in the downstream reactor section 230. In additional embodiments, a reactor configuration that is fully of a riser-type may operate at a single high superficial gas velocity, for example, in some embodiments at least 30 ft/s (about 9.15 m/s) throughout.

In additional embodiments, the ratio of catalyst to feed stream in the reactor 202 may range from 5 to 100 on a weight to weight (w/w) basis. In some embodiments, the ratio may range from 10 to 40, such as from 12 to 36, or from 12 to 24.

In additional embodiments, the catalyst flux may be from 1 pound per square foot-second (lb/ft$^2$-s) (about 4.89 kg/m$^2$-s) to 20 lb/ft$^2$-s (to about 97.7 kg/m$^2$-s) in the upstream reactor section 250, and from 10 lb/ft$^2$-s (about 48.9 kg/m$^2$-s) to 100 lb/ft$^2$-s (about 489 kg/m$^2$-s) in the downstream reactor section 230.

In operation, the catalyst may move upward through the downstream reactor section 230 (from the upstream reactor section 250), and into the separation device 220. The separated vapors may be removed from the reactor system 102 via a pipe 420 at a gas outlet port 216 of the catalyst separation section 210. According to one or more embodiments, the separation device 220 may be a cyclonic separation system, which may include two or more stages of cyclonic separation. In embodiments where the separation device 220 comprises more than one cyclonic separation stage, the first separation device into which the fluidized stream enters is referred to a primary cyclonic separation device. The fluidized effluent from the primary cyclonic separation device may enter into a secondary cyclonic separation device for further separation. Primary cyclonic separation devices may include, for example, primary cyclones, and systems commercially available under the names VSS (commercially available from UOP), LD2 (commercially available from Stone and Webster), and RS2 (commercially available from Stone and Webster). Primary cyclones are described, for example, in U.S. Pat. Nos. 4,579,716; 5,190,650; and 5,275,641, which are each incorporated by reference in their entirety herein. In some separation systems utilizing primary cyclones as the primary cyclonic separation device, one or more set of additional cyclones, e.g. secondary cyclones and tertiary cyclones, are employed for further separation of the catalyst from the product gas. It should be understood that any primary cyclonic separation device may be used in embodiments of the invention.

According to some embodiments, following separation from vapors in the separation device 220, the catalyst may generally move through the stripper 224 to the reactor catalyst outlet port 222 where the catalyst is transferred out of the reactor portion 200 via standpipe 426 and into the catalyst processing portion 300. Optionally, the catalyst may also be transferred directly back into the upstream reactor section 250 via standpipe 422. Alternatively, the catalyst may be premixed with processed catalyst in the transport riser 430.

As is described in detail in accordance with the embodiment of FIG. 1, according to one or more embodiments, the catalyst may be processed by one or more of the steps of passing the catalyst from the reactor 202 to the combustor 350, burning a supplemental fuel source or coke from the deactivated catalyst in the combustor 350, and passing the heated catalyst from the combustor 350 to the reactor 202.

Referring now to the catalyst processing portion 300, as depicted in FIG. 1, the combustor 350 of the catalyst processing portion 300 may include one or more lower reactor portion inlet ports 352 and may be in fluid communication with the riser 330. The combustor 350 may be in fluid communication with the catalyst separation section 210 via standpipe 426, which may supply spent catalyst from the reactor portion 200 to the catalyst processing portion 300 for regeneration. The combustor 350 may include an additional lower reactor section inlet port 352 where air inlet 428 connects to the combustor 350. The air inlet 428 may supply reactive gases which may react with the spent catalyst or a supplemental fuel to at least partially regenerate the catalyst. For example, the catalyst may be coked following the reactions in the upstream reactor section 250, and the coke may be removed from the catalyst (i.e., regenerating the catalyst) by a combustion reaction. For example, oxidizer (such as air) may be fed into the combustor 350 via the air inlet 428. Alternatively or additionally, such as when a substantial amount of coke is not formed on the catalyst, a supplemental fuel may be injected into the combustor 350, which may be burned to heat the catalyst. Following combustion, the processed catalyst may be separated in the catalyst separation section 310 and delivered back into the reactor portion 200 via standpipe 424.

As the catalyst is continuously recirculated through the reactor system 102, the catalyst may become permanently deactivated, such as through through loss and/or deterioration of catalytically active materials of the catalyst, such as platinum, palladium, or gallium for example. The catalyst may also become permanently deactivated through buildup of heavy metals or other contaminants in the catalyst that cannot be removed through combustion, loss of surface area of the catalyst, or blockage of active sites by chemical compounds. As used herein, the term "permanently deactivated" refers to catalyst that has insufficient catalytic activity to efficiently catalyze the conversion reactions conducted in the reaction portion and the catalytic activity cannot be increased and/or restored by raising the temperature or burning off coke deposits. That is, permanently deactivated catalysts cannot be regenerated in the combustor by normal plant operations.

The permanent deactivation rate of the catalyst may vary widely depending on the catalyst and reaction mechanism employed by the reaction system 102. For example, in a dehydrogenation system, the permanent deactivation of the dehydrogenation catalyst may occur mainly through loss of the catalytically active material (e.g., platinum, palladium, or gallium) from the surfaces of the catalyst. The loss of the catalytically active material from the surface of the dehydrogenation catalyst and permanent deactivation of the dehydrogenation catalyst may occur at a much slower rate compared to the permanent deactivation of cracking catalysts, which generally become permanently deactivated through buildup of heavy metal species on the catalyst. The slow permanent deactivation rate of the dehydrogenation catalyst in a dehydrogenation reactor system may require that the entire volume of dehydrogenation catalyst be withdrawn and replaced over a period of time greater than or equal to 9 months, such as from 9 months to 3 years, from 9 months to 2 years, from 9 months to 1 year, from 1 year to 3 years, or from 1 year to 2 years. For comparison, the higher permanent deactivation rate for cracking catalyst in a fluidized catalytic cracking system may require withdrawal and replacement of the entire volume of cracking catalyst in less than or equal to 6 months, such as from 1 month to 6 months, from 1 month to 5 months, from 1 month to 3 months, from 3 months to 6 months, from 3 months to 5 months, or from 4 months to 6 months.

Referring still to FIG. 1, the catalyst withdrawal system 500 may be coupled to the catalyst processing portion 300 of the reactor system 102 for withdrawing catalyst from the reactor system 102 continuously or batch-wise. The catalyst withdrawal system 500 may include a catalyst withdrawal vessel 502 and a transfer line 504 coupling the catalyst withdrawal system 500 to the catalyst processing portion 300 of the reactor system 102. In some embodiments, the transfer line 504 may couple the catalyst withdrawal vessel 502 to the catalyst processing portion 300 at the catalyst separation section 310 of the catalyst processing portion 300. During operation of the catalyst withdrawal system 500, catalyst may be passed from the catalyst separation section 310 of the catalyst processing portion 300 through transfer line 504 into the catalyst withdrawal vessel 502, thereby withdrawing the catalyst from the reactor system 102.

Figure 2:
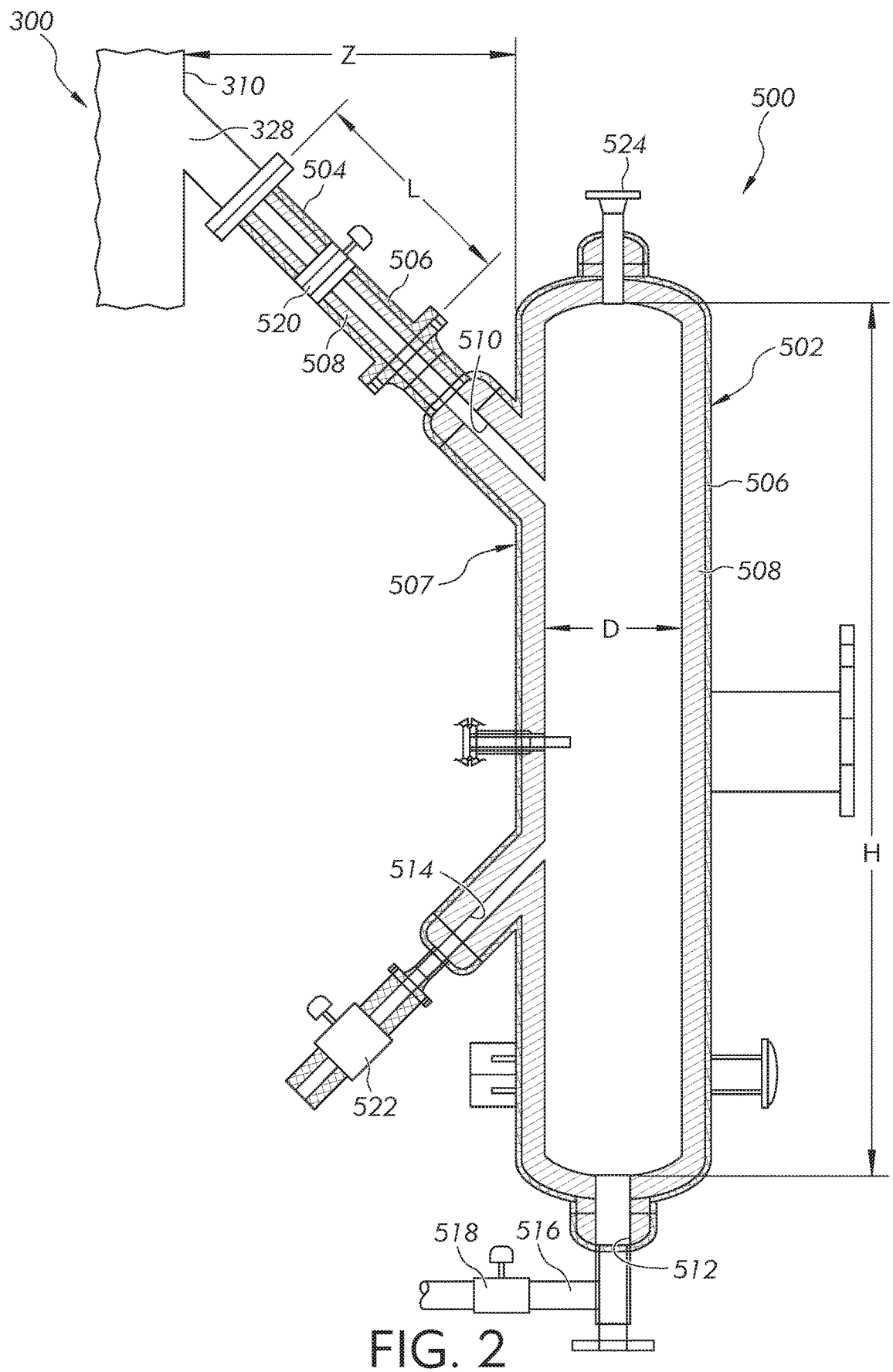
FIG. 2 schematically depicts a cross-sectional view of a catalyst withdrawal system of the reactor system of FIG. 1, according to one or more embodiments described herein.

Referring now to FIG. 2, according to one or more embodiments, the catalyst withdrawal vessel 502 may include a catalyst inlet port 510 and at least one catalyst outlet port 512. The catalyst inlet port 510 may be coupled to the transfer line 504 such that the catalyst inlet port 510 may be in fluid communication with the catalyst separation section 310 of the catalyst processing portion 300 through the transfer line 504. In some embodiments, the catalyst inlet port 510 may be positioned in a top portion of the catalyst withdrawal vessel 502. The catalyst outlet port 512 may be positioned on an opposite end of the catalyst withdrawal vessel 502 from the catalyst inlet port 510. In embodiments, the catalyst outlet port 512 may be positioned in a bottom portion of the catalyst withdrawal vessel 502. In some embodiments, the catalyst withdrawal vessel 502 may include a continuous catalyst outlet port 514. The continuous catalyst outlet port 514 may be utilized to continuously withdraw catalyst from the catalyst withdrawal vessel 502 when the catalyst withdrawal system 500 is operated in a continuous withdrawal mode. The continuous catalyst outlet port 514 may be positioned in a side of the catalyst withdrawal vessel 502 at the bottom portion of the catalyst withdrawal vessel 502. Catalyst withdrawn from the catalyst processing portion 300 into the catalyst withdrawal vessel 502 passes by gravity from the catalyst inlet port 510 in the top portion of the catalyst withdrawal vessel 502, down through the catalyst withdrawal vessel 502, and out of the catalyst outlet port 512 and/or the continuous catalyst outlet port 514, which are both positioned in the bottom of the catalyst withdrawal vessel 502.

The catalyst withdrawal vessel 502 may have an inner height H greater than an inner diameter D of the catalyst withdrawal vessel 502. The catalyst withdrawal vessel 502 may have an aspect ratio sufficient to provide enough heat transfer area to cool the catalyst in the catalyst withdrawal vessel 502 without causing the temperature of the outer metallic shell 506 to reach 350° C. According to one or more embodiments, the catalyst withdrawal vessel 502 may be designed and operated such that the catalyst is cooled to a temperature below 350° C. inside the catalyst withdrawal vessel 502 prior to being passed out of the catalyst withdrawal vessel 502. The thermal properties of the catalyst withdrawal vessel 502 and the residence time of the catalyst in the catalyst withdrawal vessel 502 are such that sufficient cooling of the catalyst is undergone prior to the catalyst being expelled from the reactor system 102. For example, hot catalyst enters the catalyst withdrawal vessel 502 and cools to less than 350° C. before it is removed from the catalyst withdrawal vessel 502. As used herein, the "aspect ratio" refers to the inner height H of the catalyst withdrawal vessel 502 divided by the inner diameter D of the catalyst withdrawal vessel 502. In some embodiments, the catalyst withdrawal vessel 502 may have an aspect ratio of greater than or equal to 2, greater than or equal to 2.5, greater than or equal to 3, or greater than or equal to 3.5.

Referring to FIG. 2, the transfer line 504 may extend from the catalyst separation section 310 of the catalyst processing portion 300 to the catalyst inlet port 510 of the catalyst withdrawal vessel 502. In some embodiments, the transfer line 504 may be coupled to a withdrawal port 328 of the catalyst separation section 310 of the catalyst processing portion 300. The transfer line 504 may extend in a downward slope from the catalyst separation section 310 of the catalyst processing portion 300 to the catalyst inlet port 510 of the catalyst withdrawal vessel 502 so that catalyst may pass by gravity through the transfer line 504 to the catalyst withdrawal vessel 502.

The transfer line 504 may close couple the catalyst withdrawal vessel 502 to the catalyst separation section 310. For example, in some embodiments, an outer wall 507 of an outer metallic shell 506 of the catalyst withdrawal vessel 502 may be positioned less than or equal to 20 feet from the catalyst separation section 310. In other embodiments, the outer wall 507 of the outer metallic shell 506 of the catalyst withdrawal vessel 502 may be less than or equal to 50 feet from the catalyst separation section 310, such as less than or equal to 40 feet, less than or equal to 30 feet, less than or equal to 20 feet, less than or equal to 15 feet, less than or equal to 10 feet, or even less than or equal to 5 feet from the catalyst separation section 310. In some embodiments, the radial distance Z between the outer wall 507 of the catalyst withdrawal vessel 502 and the catalyst separation section 310 may be less than or equal to 50 feet, less than or equal to 40 feet, less than or equal to 30 feet, less than or equal to 20 feet, less than or equal to 15 feet, less than or equal to 10 feet, or even less than or equal to 5 feet. In some embodiments, the transfer line 504 may have a length L measured from the withdrawal port 328 of the catalyst separation section 310 of the catalyst processing portion 300 to the catalyst inlet port 510 of the catalyst withdrawal vessel 502 that may be less than or equal to 50 feet, less than or equal to 40 feet, less than or equal to 30 feet, less than or equal to 20 feet, less than or equal to 15 feet, less than or equal to 10 feet, or even less than or equal to 5 feet.

Close coupling the catalyst withdrawal vessel 502 to the catalyst separation section 310 with the transfer line 504 (i.e., positioning the catalyst withdrawal vessel 502 close to the catalyst separation section 310) may reduce the distance that the catalyst travels through the transfer line 504, thus, reducing the time that the catalyst is in transfer line 504. This may reduce the exposure of the transfer line 504 to the high temperatures of the catalyst of greater than 350° C., or even greater than 680° C. Close coupling the catalyst withdrawal vessel 502 to the catalyst processing portion 300 of the reactor system 102 may also reduce the length of the transfer line 504, thus reducing the length of refractory-lined pipe required to transfer withdrawn catalyst from the catalyst processing portion 300 to the catalyst withdrawal vessel 502. In the event that replacement of the transfer line 504 becomes necessary, replacement of the transfer line 504 may be more cost effective because of the reduced length of the transfer line 504.

The transfer line 504 may include at least one flow restrictor 520 positioned between the catalyst separation section 310 and the catalyst withdrawal vessel 502. The flow restrictor 520 may be positioned to regulate and/or control the flow of the catalyst through the transfer line 504 from the catalyst separation section 310 to the catalyst withdrawal vessel 502. The flow restrictor 520 may include at least one of a valve, an orifice plate, or both. In some embodiments, the flow restrictor 520 may be a valve, such as an Everlasting valve made by the Everlasting Valve Company, for example. Other valves include gate valves, ball valves, or slide valves with vapor purges to minimize catalyst accumulation or stagnation. In other embodiments, the flow restrictor 520 may include two or more valves positioned in the transfer line. In still other embodiments, the flow restrictor 520 may include one or a plurality of orifice plates that provide a flow restriction in the transfer line 504 to limit the flow of catalyst through the transfer line 504.

Referring to FIG. 2, the catalyst withdrawal vessel 502 and the transfer line 504 may each include the outer metallic shell 506 and an inner refractory lining 508. The outer metallic shell 506 may be carbon steel, stainless steel, or other metal. The inner refractory lining 508 may be disposed inside of the outer metallic shell 506 to slow heat transfer from the hot catalyst to the outer metallic shell 506, thereby preventing the outer metallic shell 506 from heating to temperatures in excess of a deforming temperature of the outer metallic shell 506. The inner refractory lining 508 may have a thickness sufficient to maintain the temperature of the outer metallic shell 506 equal to or less than 350° C., which may prevent the outer metallic shell 506 from deforming, but may be thin enough to maintain the temperature as high as possible to enable rapid dissipation of heat from the outer metallic shell 506 of the catalyst withdrawal vessel 502 to the ambient air. Maintaining rapid dissipation of heat from the outer metallic shell 506 to the ambient air may maintain a high heat transfer rate through the inner refractory lining 508 and outer metallic shell 506, which may result in more rapid cooling of the catalyst in the catalyst withdrawal vessel 502. The thickness of the inner refractory lining 508 may depend on the thermal conductivity of the inner refractory lining 508. In some embodiments, the inner refractory lining 508 may have a thickness of greater than or equal to 1 inch, greater than or equal to 1.5 inches, greater than or equal to 2 inches, greater than or equal to 2.5 inches, or greater than or equal to 3 inches. In some embodiments, the thickness of the inner refractory lining 508 may be from 1 inch to 8 inches, from 1.5 inches to 6 inches, from 2 inches to 6 inches, from 2.5 inches to 6 inches, or from 3 inches to 6 inches.

In embodiments, the inner refractory lining 508 of the catalyst withdrawal vessel 502 may comprise a thermal shock resistant refractory material. In some other embodiments, the inner refractory lining 508 of the catalyst withdrawal vessel 502 and the transfer line 504 may comprise a thermal shock resistant refractory material. Without being bound by theory, it is belived that the thermal stress experienced by the inner refractory lining 508 may be a function of the coefficient of linear thermal expansion of the inner refractory lining 508, the temperature gradient through the inner refractory lining 508, and the thermal conductivity of the inner refractory lining 508. Without being bound by theory, it is believed that the coefficient of linear expansion and/or the thermal shock resistance may be a function of one or more of the grain structure, type of binder, heat capacity, morphology of pores, or brittleness of the refractory material. When the thermal stress exceeds the fracture strength of the inner refractory lining 508, the inner refractory lining 508 may fracture. As used herein, a "thermal shock resistant" refractory material refers to a refractory material that can mechanically withstand (e.g., not crack or significantly deteriorate) thermal cycling of a process, such as the introduction of hot catalyst and the subsequent cooling of the catalyst. For example, a thermal shock resistant material, such as a refractory lining, may not excessively crack (e.g., develop cracks having a width of at least 0.25 inches or greater) or significantly deteriorate when repeatedly heated to the temperature of the hot catalyst (e.g., greater than 680° C.) and cooled to the temperature of the withdrawn catalyst (e.g., less than 350° C.).

The thermal shock resistant refractory material may have a thermal coefficient of linear thermal expansion (CTE) that is sufficiently small to maintain the thermal stress on the inner refractory lining 508 less than the fracture strength of the inner refractory lining 508 during operation of the catalyst withdrawal system 500. Maintaining the thermal stress on the inner refractory lining 508 less than the fracture strength may reduce the probability of fracturing the inner refractory lining 508 during thermal cycling, which may reduce the cracks and/or deterioration of the inner refractory lining 508. In some embodiments, the thermal shock resistant refractory material may have a CTE that is less than or equal to $2.7 \times 10^{-6}$ per Kelvin ($K^{-1}$) (i.e., $1.5 \times 10^{-6}$ per degree Fahrenheit (° $F.^{-1}$)), or less than or equal to $1.8 \times 10^{-6}$ $K^{-1}$ (i.e., $1.0 \times 10^{-6}$° $F.^{-1}$) in other embodiments. The CTE may be determined according to ASTM E831-14.

The thermal shock resistant refractory material may also have a strength loss due to thermal cycling that is sufficiently low to enable the inner refractory lining 508 to maintain adequate strength when exposed to prolonged thermal cycling. In some embodiments, the thermal shock resistant refractory material may have a strength loss of less than or equal to 25% according to ASTM C-1171. In other embodiments, the thermal shock resistant refractory material may have a strength loss of less than or equal to 20%, less than or equal to 15%, less than or equal to 10%, or even less than or equal to 5% according to the modulus of rupture (MOR) standard described in ASTM C-1171.

The thermal shock resistant refractory material may include at least one of fused silica, vitreous silica, cordierite, or a combination of these. In some embodiments, the thermal shock resistant refractory material may consist of fused silica. Examples of shock resistant refractory materials may include, but are not limited to VIBROCAST FS-6G fused silica refractory material, SUREFLOW FS-6LC fused silica refractory material, or VIBROCAST FS-6 fused silica refractory material obtainable from RESCO® Products, Inc. The following Table 1 provides the CTE and strength loss for the above-described materials.

TABLE 1

Properties of Exemplary Shock Resistant Refractory Materials

| Shock Resistant Refractory Material | Strength Loss ($\Delta_{MOR}$ via ASTM C1171) | CTE ($\times 10^{-6}$ in/in/° C.) |
| --- | --- | --- |
| Vibrocast FS-6G | 0% | 1.4 |
| Sureflow FS-6LC | 2% | 1.4 |
| Vibrocast FS-6 | 3% | 1.4 |

The thermal shock resistant refractory material may prevent the inner refractory lining 508 of the catalyst withdrawal vessel 502, transfer line 504, or both, from cracking due to excessive thermal stress caused by thermal cycling (i.e., heating up and cooling down of the catalyst withdrawal system 500), such as when the catalyst withdrawal system 500 is used to withdraw catalyst from the catalyst separation section 310 in batch operation of the catalyst withdrawal system 500. Use of the thermal shock resistant refractory material may reduce the loss of strength of the inner refractory lining 508 that may be caused from continuous and repeated thermal cycling. Maintaining the strength of the inner refractory lining 508 may prevent cracking and deterioration of the inner refractory lining 508 over time as the catalyst withdrawal system 500 experiences thermal cycling over multiple catalyst withdrawal cycles.

Still referring to FIG. 2, at least a portion of the catalyst may be withdrawn from the catalyst processing portion 300 of the reactor system 102 into the catalyst withdrawal system 500 batch-wise during operation of the reactor system 102. During batch operation of the catalyst withdrawal system 500, the catalyst may pass from the catalyst separation section 310 of the catalyst processing portion 300, through the transfer line 504, and into the catalyst withdrawal vessel 502 through the catalyst inlet port 510. The catalyst withdrawn from the catalyst separation section 310 may be at a temperature of greater than 680° C., such as from 680° C. to 800° C. The catalyst may accumulate in the catalyst withdrawal vessel 502. The catalyst may be maintained in the catalyst withdrawal vessel 502 as the catalyst cools. The catalyst in the catalyst withdrawal vessel 502 may be cooled through conduction of heat through the inner refractory lining 508 and the outer metallic shell 506 and transfer of heat to the ambient air through thermal convection and/or radiation from the outer surface of the outer metallic shell 506. During operation of the catalyst withdrawal system 500, the outer metallic shell 506 of the catalyst withdrawal vessel 502 may have a temperature of less than or equal to 350° C. In some embodiments, the catalyst may be held in the catalyst withdrawal vessel 502 until the temperature of the catalyst cools from greater than or equal to 680° C. to less than or equal to 350° C. In some embodiments, a residence time of the catalyst in the catalyst withdrawal vessel 502 may be a time suitable to allow for the catalyst to cool to temperature of less than or equal 350° C. For example, the residence time of the catalyst in the catalyst withdrawal vessel 502 may be sufficient to cool the catalyst from greater than or equal to 680° C. to less than or equal to 350° C. For example, without limitation, the residence time may be from 15 minutes to several weeks, such as from 30 minutes to 24 hours or from 1 hour to 12 hours. In some embodiments, the catalyst may be cooled by heat transfer through the inner refractory lining 508 and outer metallic shell 506 of the catalyst withdrawal vessel 502 without additional active cooling of the catalyst, such as quenching the catalyst or employing a heat exchanger, for example.

Once the catalyst in the catalyst withdrawal vessel 502 cools to less than or equal to 350° C., the catalyst may be withdrawn from the catalyst withdrawal vessel 502 through the catalyst outlet port 512. The catalyst may be discharged to a catalyst hopper (not shown) or other container, such as a portable tote bin, drums, or other containers. Alternatively, in some embodiments, the catalyst may be discharged to another process, such as but not limited to a catalyst classifier 600 (FIG. 4) or catalyst re-impregnation system 620 (FIG. 5), for example.

In some processes conducted in the reactor system 102, permanent deactivation of the catalyst may not develop rapidly and very little catalyst may need to be withdrawn from the reactor system 102 per unit time. In these circumstances, batch withdrawal of the catalyst from the catalyst separation section 310 of the catalyst processing portion 300 may be more advantageous given that the slow deactivation rate of the catalyst may provide sufficient time for the withdrawn catalyst to remain in the catalyst withdrawal vessel 502 to cool.

In other processes conducted in the reactor system 102, permanent deactivation of the catalyst may develop more rapidly, which may necessitate more rapid withdrawal of the catalyst from the reactor system 102. In these embodiments, the catalyst withdrawal system 500 may also be operated to continuously withdraw catalyst from the catalyst separation section 310. As used herein, "continuous" can refer to fully-continuous or semi-continuous operation. As described herein, fully-continuous operation refers to constant withdrawal of catalyst during the time that the reaction system 102 is operating. For example, the catalyst may be withdrawn from the catalyst processing portion 300 of the reactor system 102 into the catalyst withdrawal system 500 continuously during operation of the reactor system 102. As used herein, semi-continuous refers to withdrawing catalyst for a period of time on a periodic basis. For example, catalyst may be passed into the catalyst withdrawal system 500 for a set period of time per hour, day, or week, and repeated each hour, day, week. For example, semi-continuous operation could include passing catalyst into and out of the catalyst withdrawal system 500 for 10 minutes each hour, and repeated each hour during operation. During the remaining time in the hour, withdrawal may be stopped. For example, in semi-continuous operation, the catalyst withdrawal system 500 may be operated in a continuous manner to withdraw catalyst from the catalyst processing portion 300 of the reactor system 102 during the first period of time, such as 5 minutes, within a second period of time, such as 1 hour. During the first period, the catalyst withdrawal system 500 may operate to continuously withdraw catalyst from the catalyst processing portion 300 into the catalyst withdrawal vessel 502, and catalyst may be continuously removed from the catalyst withdrawal vessel 502. At the end of the first period, continuous operation of the catalyst withdrawal system 500 may be stopped and the catalyst may be retained in the catalyst withdrawal vessel 502 until the end of the second period. At the end of the second period, operation of the catalyst withdrawal vessel 502 may switch back to continuous operation for the first period and then switch back to no withdrawal during the remainder of the second period, and so forth. In another example, the first period may be 2 hours and the second period may be one day. In still another example, the first period may be one day and the second period may be one week. Other periods of time are contemplated for the first time period and second time period.

Referring to FIG. 2, in continuous or semi-continuous operation, catalyst withdrawn from the catalyst separation section 310 may pass through the transfer line 504 and into the catalyst withdrawal vessel 502 through the catalyst inlet port 510. The flow rate of the catalyst through the transfer line 504 from the catalyst separation section 310 to the catalyst withdrawal vessel 502 may be controlled using the flow restrictor 520 positioned in the transfer line 504. In some embodiments, the catalyst may pass through the transfer line 504 and into the catalyst withdrawal vessel 502 at a very slow mass flow rate. The catalyst may be continuously passed out of the catalyst withdrawal vessel 502 through the continuous catalyst outlet port 514, which may be positioned in a side of the catalyst withdrawal vessel 502. In continuous withdrawal operation, catalyst may be continuously passed into the catalyst withdrawal vessel 502, through the catalyst withdrawal vessel 502, and back out of the catalyst withdrawal vessel 502 through the continuous catalyst outlet port 514.

The continuous catalyst outlet port 514 may be coupled to at least one catalyst outlet flow restrictor 522 positioned to control a flow rate of catalyst out of the continuous catalyst outlet port 514 of the catalyst withdrawal vessel 502. In some embodiments, the catalyst outlet flow restrictor 522 may be a valve, such as an Everlasting valve made by the Everlasting Valve Company, for example. Other valves may include gate valves, ball valves, or slide valves with vapor purges to minimize catalyst accumulation or stagnation. In other embodiments, the catalyst outlet flow restrictor 522 may include two or more valves positioned in the continuous catalyst outlet port 514. The flow rate of the catalyst through the catalyst outlet flow restrictor 522 may be adjusted to adjust the accumulation of catalyst within the catalyst withdrawal vessel 502 during continuous operation of the catalyst withdrawal system 500.

During continuous or semi-continuous operation of the catalyst withdrawal system 500, a residence time of the catalyst in the catalyst withdrawal vessel 502 may be a time suitable to allow for the catalyst to cool to temperature of less than or equal 350° C. For example, the residence time of the catalyst in the catalyst withdrawal vessel 502 may be sufficient to cool the catalyst from greater than or equal to 680° C. to less than or equal to 350° C. For example, without limitation, the residence time may be from 15 minutes to several weeks, such as from 30 minutes to 24 hours or from 1 hour to 12 hours. The catalyst passing into and out of the catalyst withdrawal vessel 502 may have a hourly space velocity sufficient to cool the catalyst from greater than or equal to 680° C. to less than or equal to 350° C. The hourly space velocity is the mass flow rate of the catalyst through the catalyst withdrawal vessel 502 divided by the mass of catalyst in the catalyst withdrawal vessel 502. The hourly space velocity is reported in mass of catalyst per hour per mass of catalyst in the catalyst withdrawal vessel 502 (e.g., lb of flow/hr/lb). In some embodiments, the catalyst withdrawal system 500 may have an average hourly space velocity of catalyst through the catalyst withdrawal vessel 502 of from 0.05 lb of flow/hr/lb to 1.0 lb of flow/hr/lb. For semi-continuous operation, the average hourly space velocity of catalyst through the catalyst withdrawal vessel 502 is taken over the on and off times (i.e., for the entire duration of the second time period, which includes the first period of continuous operation.)

Once the catalyst in the catalyst withdrawal vessel 502 is cooled to less than or equal to 350° C., the catalyst may be withdrawn from the catalyst withdrawal vessel 502 through either the catalyst outlet port 512 (batch withdrawal) or the continuous catalyst outlet port 514 (continuous withdrawal). Withdrawing the catalyst from the catalyst withdrawal vessel 502 may remove the catalyst from the reactor system 102.

In embodiments, the catalyst withdrawal vessel 502 may be configured to pass a fluid through the catalyst withdrawal vessel 502 and the catalyst contained within the catalyst withdrawal vessel 502. Referring to FIG. 2, for example, the catalyst withdrawal vessel 502 may have a fluid inlet port 516 and a fluid inlet valve 518. In some embodiments, the fluid inlet port 516 may be positioned at or adjacent to the catalyst outlet port 512 so that the fluid may pass into the catalyst withdrawal vessel 502 through catalyst outlet port 512. Other positions for fluid inlet port 516 are contemplated. The fluid may be a gas, such as nitrogen, argon, air, steam, other gas stream, or combinations of these. The fluid may have a temperature less than the temperature of the catalyst passed from the catalyst separation section 310 into the catalyst withdrawal vessel 502. In some embodiments, the fluid may have a temperature less than 350° C. In embodiments, the fluid passing into the catalyst withdrawal vessel 502 through the fluid inlet port 516 may pass through the catalyst in the inner volume of the catalyst withdrawal vessel 502 and through the transfer line 504 into the catalyst separation section 310. The fluid may then pass out of the catalyst separation section 310 of the catalyst processing portion 300 with the gasses produced in the catalyst processing portion 300 of the reactor system 102 (e.g., flue gas). Alternatively, in other embodiments, the catalyst withdrawal vessel 502 may have a fluid outlet 524 positioned near a top portion of the catalyst withdrawal vessel 502 such that the fluid may pass into the catalyst withdrawal vessel 502 through the fluid inlet valve 518, passes through the catalyst withdrawal vessel 502 and the catalyst contained therein, and may pass out of the catalyst withdrawal vessel 502 through the fluid outlet 524.

In some embodiments, the fluid inlet valve 518 may be a three way valve. The fluid inlet valve 518 may be controlled to control a flow rate of the fluid through the catalyst withdrawal vessel 502 and the catalyst contained in the catalyst withdrawal vessel 502. As previously described, the catalyst withdrawal system 500 may be configured so that the fluid passes through the fluid inlet port 516 and into the catalyst withdrawal vessel 502 and passes out of the catalyst withdrawal vessel 502 through the transfer line 504 and into the catalyst separation section 310 of the catalyst processing portion 300. During batch operation of the catalyst withdrawal system 500, the fluid inlet valve 518 may be capable of adjusting the flow rate of the fluid through the catalyst withdrawal vessel 502 between at least two flow rates. For example, when not actively withdrawing catalyst from the catalyst separation section 310 of the catalyst processing portion 300, the flow rate of the fluid through the catalyst withdrawal vessel 502 may be set to a first fluid flow rate. When the fluid is directed from the catalyst withdrawal vessel 502 through transfer line 504 and into catalyst separation section 310 of the catalyst processing portion 300, the first fluid flow rate through the catalyst withdrawal vessel 502 may be sufficient to prevent catalyst from passing from the catalyst separation section 310 into the transfer line 504. However, the first fluid flow rate may be less than a flow rate at which the fluid causes the catalyst in the catalyst withdrawal vessel 502 to pass back through the transfer line 504 to the catalyst separation section 310. When batch operation shifts to withdrawing catalyst from the catalyst separation section 310, the fluid inlet valve 518 may be controlled to reduce the flow rate of the fluid passing through the catalyst withdrawal vessel 502 to a second fluid flow rate. The second fluid flow rate may be sufficiently reduced relative to the first fluid flow rate to enable catalyst to pass by gravity from the catalyst separation section 310 into the transfer line 504. Once batch withdrawal of catalyst from the catalyst separation section 310 into the catalyst withdrawal vessel 502 is complete, the flow rate of the fluid may be returned to the first fluid flow rate to prevent further catalyst from being withdrawn from the catalyst separation section 310.

In some embodiments, the fluid inlet valve 518 may be a control valve. During continuous operation of the catalyst withdrawal system 500, the fluid inlet valve 518 may be controlled to further control the flow rate of catalyst passing from the catalyst separation section 310 through the transfer line 504 and into the catalyst withdrawal vessel 502. For example, the fluid inlet valve 518 may be controlled to reduce the flow rate of fluid through the catalyst withdrawal vessel 502, which may result in an increase in the flowrate of the catalyst passing from the catalyst separation section 310, through the transfer line 504, and into the catalyst withdrawal vessel 502. Alternatively, the fluid inlet valve 518 may be controlled to increase a flow rate of the fluid into the catalyst withdrawal vessel 502, which may result in a decrease in the flowrate of the catalyst passing from the catalyst separation section 310, through the transfer line 504, and into the catalyst withdrawal vessel 502.

Figure 3:
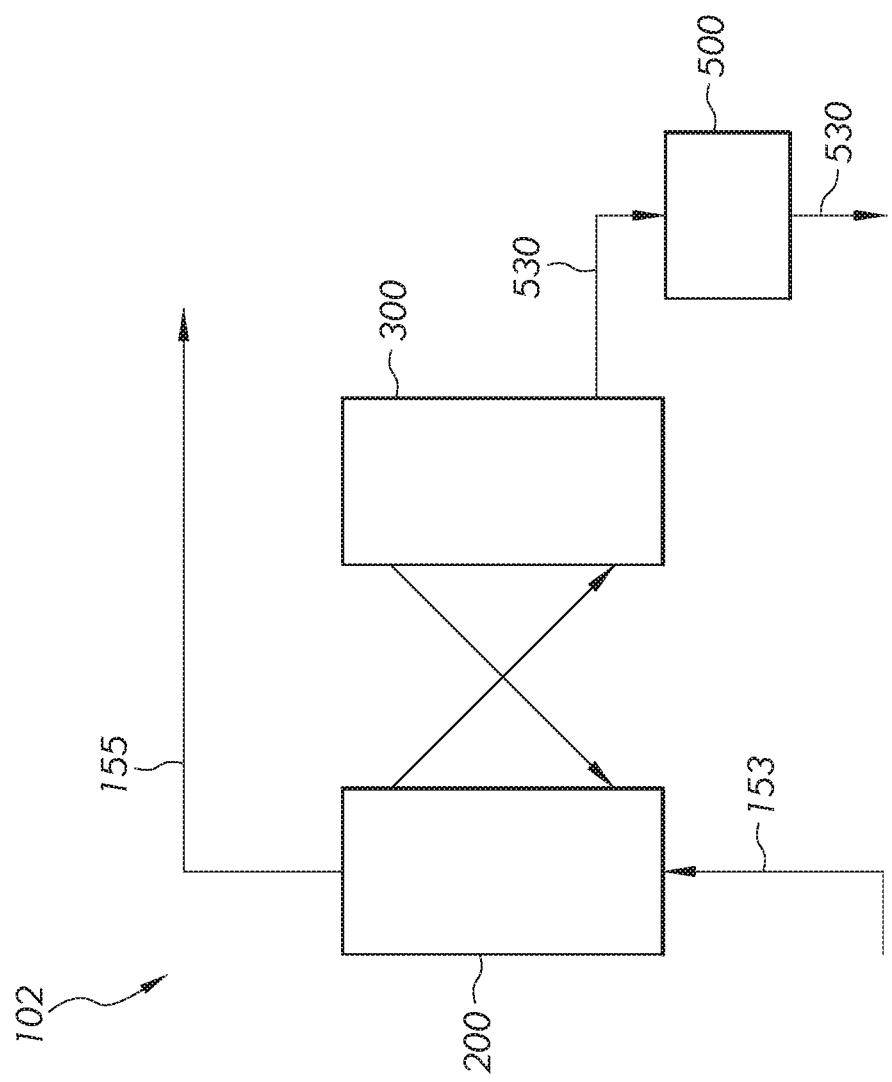
FIG. 3 schematically depicts a reaction system flow chart, according to one or more embodiments described herein.

Referring to FIG. 3, a reactor system flowchart for processing a chemical stream in the reactor system 102 is schematically depicted. As previously discussed, the reactor system 102 may be used to process a chemical stream (i.e., feed stream 153) to produce a product stream 155 having one or more chemical products, such as light olefins, for example. A method of processing the chemical stream in the reactor system 102 may include contacting the feed stream 153 with a catalyst in the reactor portion 200 of the reactor system 102. The reactor system 102 may comprise the reactor portion 200 and the catalyst processing portion 300 and contacting the feed stream 153 with the catalyst may cause a reaction which forms the product stream 155. The method may further include separating at least a portion of the product stream 155 from the catalyst, passing the catalyst to the catalyst processing portion 300 of the reactor system 102, and processing the catalyst in the catalyst processing portion 300 of the reactor system 102. Processing the catalyst in the catalyst processing portion 300 may include raising the temperature of the catalyst, removing coke deposits from the catalyst, or both in the combustor 350 of the catalyst processing portion 300 of the reactor system 102. The method may further include passing at least a portion of the catalyst 530 from the catalyst processing portion 300 of the reactor system 102 into the catalyst withdrawal system 500. As previously discussed, the catalyst withdrawal system 500 may comprise the catalyst withdrawal vessel 502 and the transfer line 504 coupling the catalyst withdrawal vessel 502 to the catalyst processing portion 300. The catalyst withdrawal vessel 502 and the transfer line 504 may each comprise the outer metallic shell 506 and the inner refractory lining 508. In embodiments, the inner refractory lining 508 of the catalyst withdrawal vessel 502 may comprise the thermal shock resistant refractory material. In embodiments, the thermal shock resistant refractory material may include at least one of fused silica vitreous silica, cordierite, or combinations of these. The catalyst withdrawn from the catalyst processing portion 300 may have a temperature of at least 680° C. The method may further comprise cooling the catalyst 530 in the catalyst withdrawal vessel 502 from greater than or equal to 680° C. to less than or equal to 350° C.

The method may further comprise withdrawing at least a portion of the catalyst 530 from the catalyst withdrawal vessel 502. As previously described, withdrawing the catalyst 530 from the catalyst withdrawal vessel 502 may remove the catalyst 530 from the reactor system 102. The catalyst withdrawal system 500 may further include a classifier 600, a re-impregnation system 620, or a classifier 600 and a re-impregnation system 620 positioned downstream of the catalyst withdrawal vessel 502. The catalyst 530 may be passed to the classifier 600, the re-impregnation system 620, or both for further processing downstream of the catalyst withdrawal vessel 502.

Figure 4:
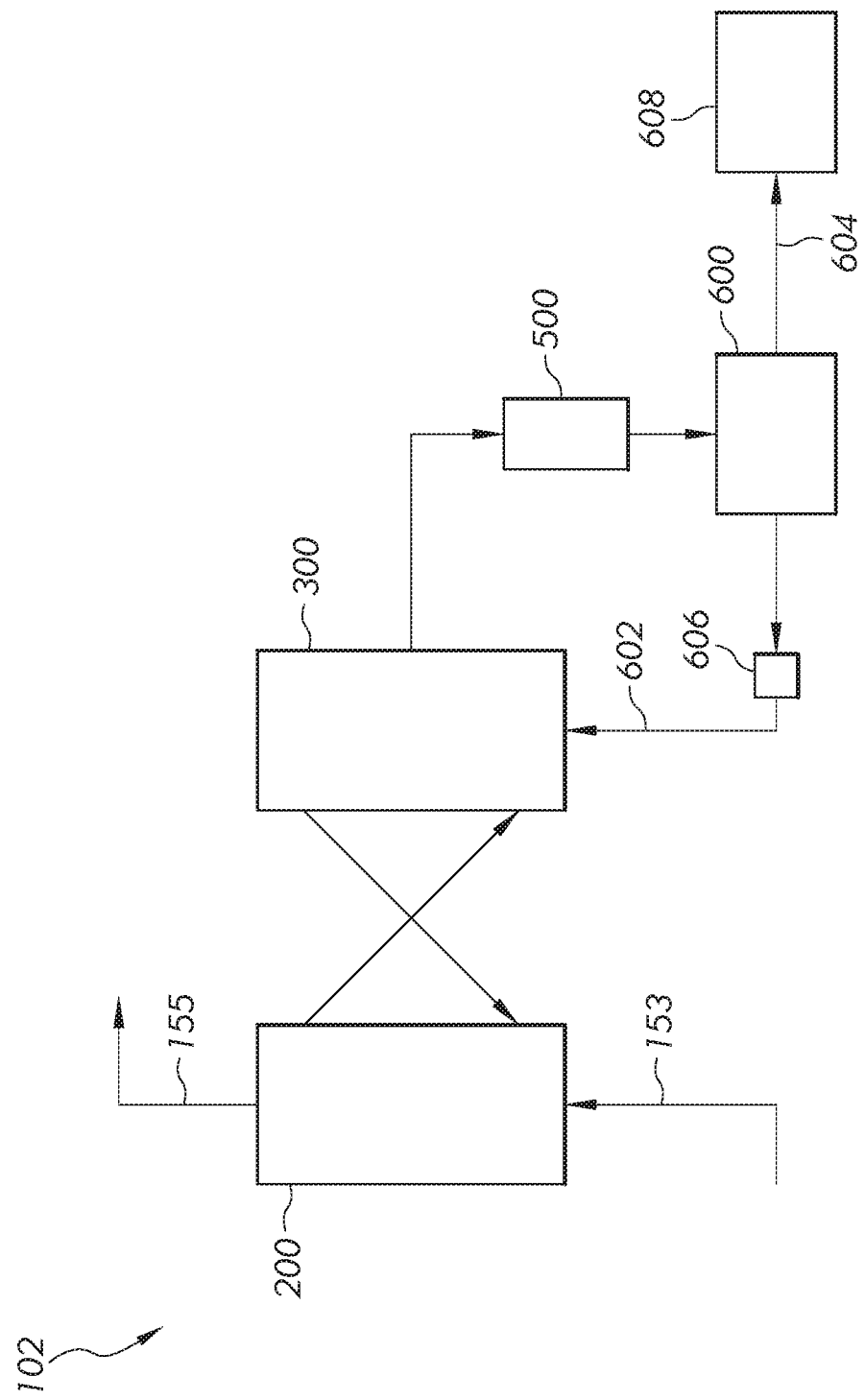
FIG. 4 schematically depicts another reaction system flow chart, according to one or more embodiments described herein.

Referring to FIG. 4, in some embodiments, the catalyst withdrawal system 500 may include the classifier 600 positioned downstream of the catalyst withdrawal vessel 502. The catalyst 530 may be passed from the catalyst withdrawal vessel 502 to the classifier 600. The classifier 600 may separate the catalyst 530 into a smaller particle-size catalyst 602 and a larger particle-size catalyst 604, wherein the larger particle-size catalyst 604 has an average particle size that may be greater than the average particle size of the smaller particle-size catalyst 602. In some embodiments, the smaller particle-size catalyst 602 may be passed back to the reactor system 102, and the larger particle-size catalyst 604 may be removed from the reactor system 102. As shown in FIG. 4, the smaller particle-size catalyst 602 may be passed back to the catalyst processing portion 300 of the reactor system 102. Alternatively, the smaller particle-size catalyst 602 may be passed back to the reactor portion 200 of the reactor system 102.

Figure 6:
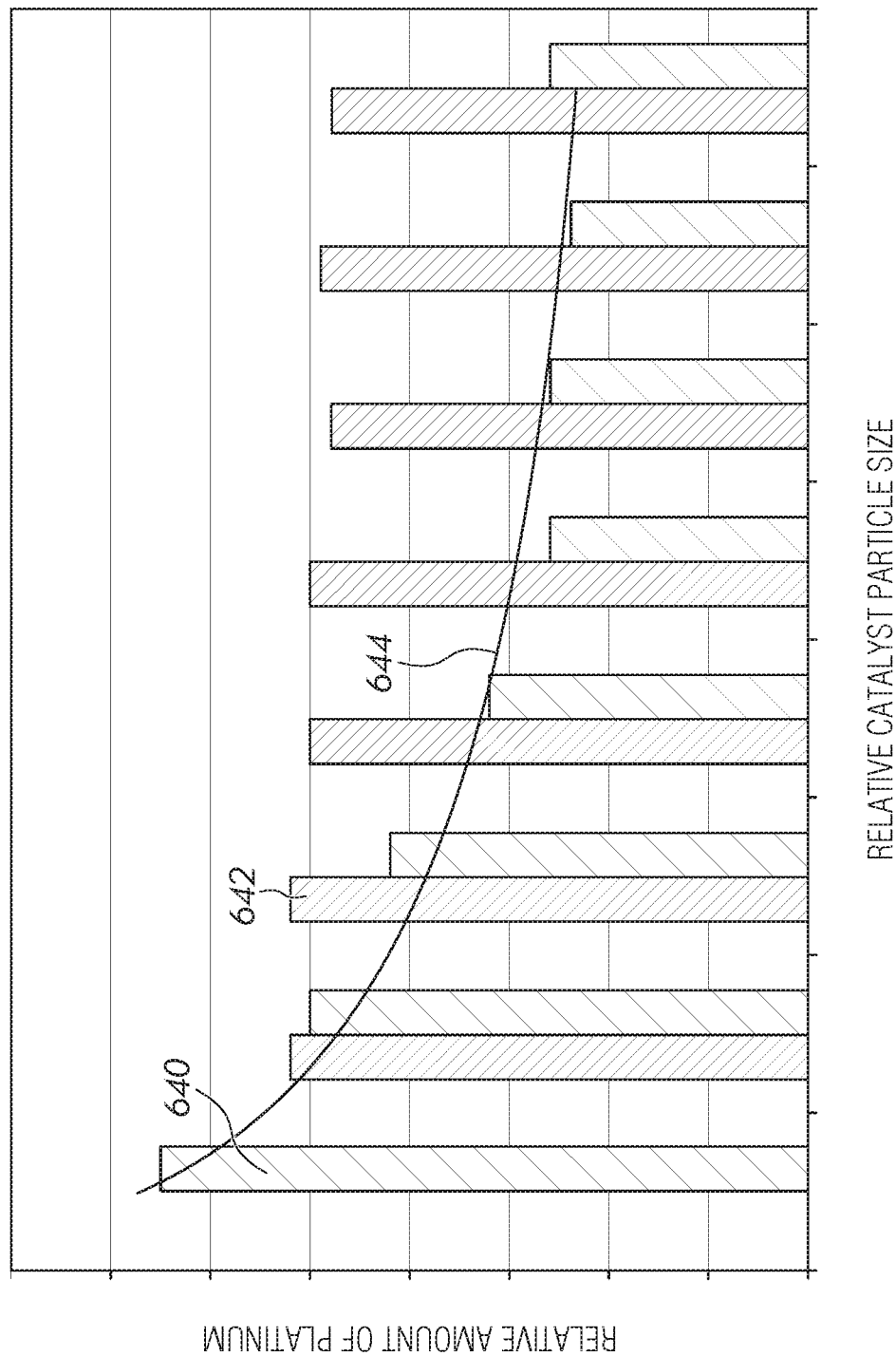
FIG. 6 schematically depicts a graph of platinum content as a function of particle size for a hydrogenation catalyst, according to one or more embodiments described herein.

It has been discovered that catalyst fines present in the smaller particle-size catalyst 602 may contain a greater amount of a catalytically active material (e.g., platinum, palladium, gallium, or other material) than the larger particle-size catalyst 604. Referring to FIG. 6, the relative amount of platinum in a dehydrogenation catalyst is shown as a function of the particle size of the catalyst for a used catalyst 640 and a new catalyst 642. As illustrated in FIG. 6, for the used catalyst 640, the relative amount of platinum may be greatest for the smallest sized catalyst particles and may decrease with increasing average particle size of the catalyst. Trend line 644 further illustrates the decreasing relative amount of platinum with increasing average particle size for the used catalyst. For the new catalyst 642, the relative amount of platinum in the catalyst is consistent relative to particle size. The increased relative amount of platinum in the used catalyst 640 having smaller average particle size has been shown to result in improved conversion of the feed stream 153 compared to the used catalyst 640 having larger average particle size.

Referring again to FIG. 4, the smaller particle-size catalyst 602 may have a smaller average particle size compared to the larger particle-size catalyst 604 and may, therefore, be expected to have a greater amount of platinum or other catalytically active material compared to the larger particle-size catalyst 604. Therefore, the smaller particle-size catalyst 602 may be passed back to the reactor system 102 to enhance the reaction of the feed stream 153 with the catalyst to produce the product stream 155. A valve 606 or other back pressure device may be installed to regulate the flow of the smaller particle-size catalyst 602 back to the reactor system 102, which may further regulate the flow of the continuous or semi-continuous batch withdrawal. The larger particle-size catalyst 604 may be removed from the classifier 600, thus, removing the larger particle-size catalyst 604 from the reactor system 102. The larger particle-size catalyst 604 may be passed to a collection vessel 608, from which the larger particle-size catalyst 604 may be passed for further processing.

Figure 5:
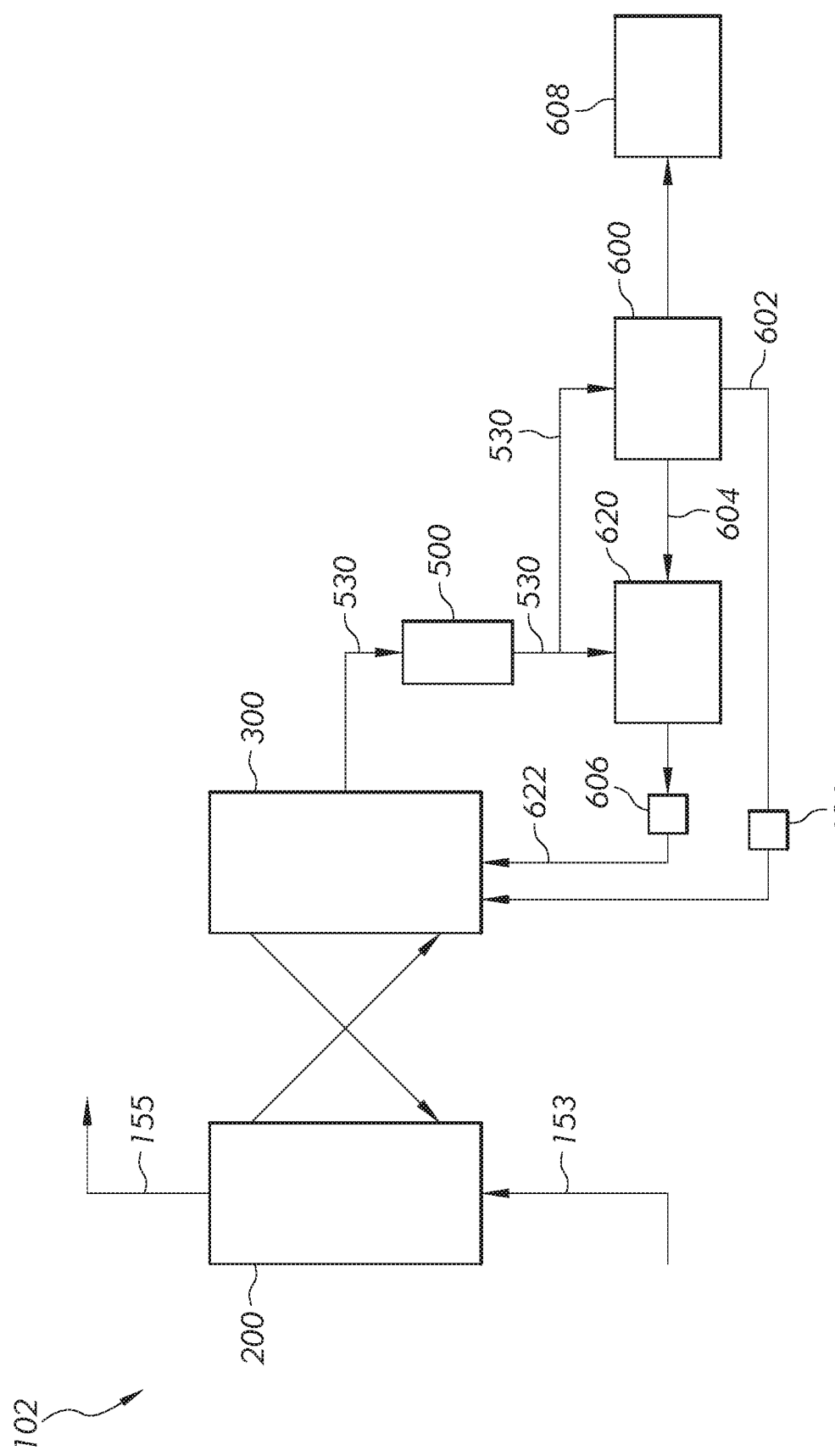
FIG. 5 schematically depicts yet another reaction system flow chart, according to one or more embodiments described herein.

Referring to FIG. 5, in some embodiments, the catalyst 530 withdrawn from the catalyst withdrawal vessel 502 may be passed to a re-impregnation system 620. In the re-impregnation system 620, the catalyst 530 withdrawn from the catalyst withdrawal vessel 502 may be re-impregnated with the catalytically active material, such as platinum, palladium, or gallium for example, to produce a re-impregnated catalyst 622. The re-impregnated catalyst 622 may then be passed back to the reactor system 102. A valve 606 or other back pressure device may be installed to regulate the flow of the smaller particle-size catalyst 602 back to the reactor system 102, which may further regulate the flow of the continuous or semi-continuous batch withdrawal. In some embodiments, the re-impregnation system 620 may apply the additional catalytically active material to the catalyst through incipient wetness impregnation process. In some of these embodiments, the catalyst having the additional catalytically active material applied thereto through the incipient wetness impregnation may be passed to the catalyst processing portion 300 of the reactor system 102 for calcination of the catalyst.

Alternatively, in other embodiments also illustrated in FIG. 5, the catalyst 530 withdrawn from the catalyst withdrawal vessel 502 may be passed to the classifier 600. In the classifier 600, the catalyst 530 withdrawn from the catalyst withdrawal vessel 502 may be separated into the smaller particle-size catalyst 602 and the larger particle-size catalyst 604. The smaller particle-size catalyst 602 may be passed back to the reactor system 102. The valve 606 or other back pressure device may be installed to regulate the flow of the smaller particle-size catalyst 602 back to the reactor system 102, which may further regulate the flow of the continuous or semi-continuous batch withdrawal. The larger particle-size catalyst 604 may be passed to the re-impregnation system 620, wherein the larger particle-size catalyst 604 may be re-impregnated with the catalytically active material (e.g., platinum, palladium, gallium, etc.) to form a re-impregnated catalyst 622. In embodiments, the re-impregnated catalyst 622 may be passed to the reactor system 102. In some embodiments, at least a portion of the larger-size catalyst 604 may be passed to the vessel 608 for further processing.

Referring to FIG. 2, in some embodiments, an apparatus for withdrawing catalyst from a reactor system 102 for processing a chemical stream may include the catalyst withdrawal vessel 502 and the transfer line 504. The catalyst withdrawal vessel 502 and the transfer line 504 may each comprise the outer metallic shell 506 and the inner refractory lining 508. The inner refractory lining 508 of the catalyst withdrawal vessel 502 may be the thermal shock resistant refractory material, as previously described herein. The catalyst withdrawal vessel 502 may include the catalyst inlet port 510 positioned in the top portion of the catalyst withdrawal vessel 502 and the catalyst outlet port 512 positioned in the bottom of the catalyst withdrawal vessel 502. In some embodiments, the catalyst inlet port 510 may be positioned in a side of the catalyst withdrawal vessel 502 at the top portion of the catalyst withdrawal vessel 502. In some embodiments, the catalyst outlet port 512 may be positioned in the bottommost portion of the catalyst withdrawal vessel 502. The transfer line 504 may include a flow restrictor 520, which may include at least one of a valve, orifice plate, or combinations of these. The transfer line 504 may be coupled to the catalyst inlet port 510 of the catalyst withdrawal vessel 502 and may extend generally upward and outward from the catalyst inlet port 510 of the catalyst withdrawal vessel 502. In some embodiments, the catalyst withdrawal vessel 502 may also have the continuous catalyst outlet port 514, which may be positioned in the side of the catalyst withdrawal vessel 502 at the bottom portion of the catalyst withdrawal vessel 502. The continuous catalyst outlet port 514 may extend generally downward and outward from the catalyst withdrawal vessel 502.

According to one or more embodiments, the reaction may be a dehydrogenation reaction. According to such embodiments, the feed stream may comprise one or more of ethane, propane, n-butane, and i-butane. For example, if the reaction is a dehydrogenation reaction, then the feed stream may comprise one or more of ethane, propane, n-butane, and i-butane. According to one or more embodiments, the feed stream may comprise at least 50 wt. %, at least 60 wt. %, at least 70 wt. %, at least 80 wt. %, at least 90 wt. %, at least 95 wt. % or even at least 99 wt. % of ethane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of propane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of n-butane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of i-butane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of the sum of ethylbenzene, ethane, propane, n-butane, and i-butane.

In one or more embodiments, a dehydrogenation reaction may utilize gallium and/or platinum catalyst as a catalyst. In such embodiments, the catalyst may comprise a gallium and/or platinum catalyst. For example, if the reaction is a dehydrogenation reaction, then the catalyst may comprise gallium and/or platinum catalyst. As described herein, a gallium and/or platinum catalyst comprises gallium, platinum, or both. The gallium and/or platinum catalyst may be carried by an alumina or alumina silica support, and may optionally comprise potassium. Such gallium and/or platinum catalysts are disclosed in U.S. Pat. No. 8,669,406, which is incorporated herein by reference in its entirety. However, it should be understood that other suitable catalysts may be utilized to perform the dehydrogenation reaction.

According to one or more embodiments, the reaction may be a cracking reaction. According to such embodiments, the feed stream may comprise one or more of naphtha, n-butane, or i-butane. For example, if the reaction is a cracking reaction, then the feed stream may comprise one or more of naphtha, n-butane, or i-butane. According to one or more embodiments, the feed stream may comprise at least 50 wt.

%, at least 60 wt. %, at least 70 wt. %, at least 80 wt. %, at least 90 wt. %, at least 95 wt. % or even at least 99 wt. % of naphtha. In additional embodiments, the feed stream may comprise at least 50 wt. %, at least 60 wt. %, at least 70 wt. %, at least 80 wt. %, at least 90 wt. %, at least 95 wt. % or even at least 99 wt. % of n-butane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of i-butane. In additional embodiments, the feed stream may comprise at least 50 wt. %, at least 60 wt. %, at least 70 wt. %, at least 80 wt. %, at least 90 wt. %, at least 95 wt. % or even at least 99 wt. % of the sum of naphtha, n-butane, and i-butane.

In one or more embodiments, a cracking reaction may utilize one or more zeolites as a catalyst. In such embodiments, the catalyst may comprise one or more zeolites. For example, if the reaction is a cracking reaction, then the catalyst may comprise one or more zeolites. In some embodiments, the one or more zeolites utilized in the cracking reaction may comprise a ZSM-5 zeolite. However, it should be understood that other suitable catalysts may be utilized to perform the cracking reaction. For example, suitable catalysts that are commercially available may include Intercat Super Z Excel or Intercat Super Z Exceed. In additional embodiments, the cracking catalyst may comprise, in addition to a catalytically active material, platinum. For example, the cracking catalyst may include from 0.001 wt. % to 0.05 wt. % of platinum. The platinum may be sprayed on as platinum nitrate and calcined at an elevated temperature, such as around 700° C. Without being bound by theory, it is believed that the addition of platinum to the catalyst may allow for easier combustion of supplemental fuels, such as methane.

According to one or more embodiments, the reaction may be a dehydration reaction. According to such embodiments, the feed stream may comprise one or more of ethanol, propanol, or butanol. For example, if the reaction is a dehydration reaction, then the feed stream may comprise one or more of ethanol, propanol, or butanol. According to one or more embodiments, the feed stream may comprise at least 50 wt. %, at least 60 wt. %, at least 70 wt. %, at least 80 wt. %, at least 90 wt. %, at least 95 wt. % or even at least 99 wt. % of ethanol. In additional embodiments, the feed stream may comprise at least 50 wt. %, at least 60 wt. %, at least 70 wt. %, at least 80 wt. %, at least 90 wt. %, at least 95 wt. % or even at least 99 wt. % of propanol. In additional embodiments, the feed stream may comprise at least 50 wt. %, at least 60 wt. %, at least 70 wt. %, at least 80 wt. %, at least 90 wt. %, at least 95 wt. % or even at least 99 wt. % of butanol. In additional embodiments, the feed stream may comprise at least 50 wt. %, at least 60 wt. %, at least 70 wt. %, at least 80 wt. %, at least 90 wt. %, at least 95 wt. % or even at least 99 wt. % of the sum of ethanol, propanol, and butanol.

In one or more embodiments, a dehydration reaction may utilize one or more acid catalysts. In such embodiments, the catalyst may comprise one or more acid catalysts. For example, if the reaction is a dehydration reaction, then the catalyst may comprise one or more acid catalysts. In some embodiments, the one or more acid catalysts utilized in the dehydration reaction may comprise a zeolite (such as ZSM-5 zeolite), alumina, amorphous aluminosilicate, acid clay, or combinations thereof. For example, commercially available alumina catalysts which may be suitable, according to one or more embodiments, include SynDol (available from Scientific Design Company), V200 (available from UOP), or P200 (available from Sasol). Commercially available zeolite catalysts which may be suitable include CBV 8014, CBV 28014 (each available from Zeolyst). Commercially available amorphous aluminosilicate catalysts which may be suitable include silica-alumina catalyst support, grade 135 (available from Sigma Aldrich). However, it should be understood that other suitable catalysts may be utilized to perform the dehydration reaction.

According to one or more embodiments, the reaction may be a methanol-to-olefin reaction. According to such embodiments, the feed stream may comprise methanol. For example, if the reaction is a methanol-to-olefin reaction, then the feed stream may comprise methanol. According to one or more embodiments, the feed stream may comprise at least 50 wt. %, at least 60 wt. %, at least 70 wt. %, at least 80 wt. %, at least 90 wt. %, at least 95 wt. % or even at least 99 wt. % of methanol.

In one or more embodiments, a methanol-to-olefin reaction may utilize one or more zeolites as a catalyst. In such embodiments, the catalyst may comprise one or more zeolites. For example, if the reaction is a methanol-to-olefin reaction, then the catalyst may comprise one or more zeolites. In some embodiments, the one or more zeolites utilized in the methanol-to-olefin reaction may comprise a one or more of a ZSM-5 zeolite or a SAPO-34 zeolite. However, it should be understood that other suitable catalysts may be utilized to perform the methanol-to-olefin reaction.

For the purposes of describing and defining the present invention it is noted that the term "about" is utilized herein to represent the inherent degree of uncertainty that may be attributed to any quantitative comparison, value, measurement, or other representation. The term is also utilized herein to represent the degree by which a quantitative representation may vary from a stated reference without resulting in a change in the basic function of the subject matter at issue.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the reactor system 102 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the reactor system 102 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combinations and variations of the disclosed embodiments incorporating the spirit and substance of the invention may occur to persons skilled in the art, the invention should be construed to include everything within the scope of the appended claims and their equivalents.

The invention claimed is:

1. A method for processing a chemical stream, the method comprising:
   contacting a feed stream with a catalyst in a reactor portion of a reactor system, wherein the reactor system comprises the reactor portion and a catalyst processing portion and the contacting of the feed stream with the catalyst causes a reaction which forms a product stream comprising a product and a spent catalyst;
   passing the spent catalyst to the catalyst processing portion of the reactor system;
   processing the spent catalyst in the catalyst processing portion of the reactor system, wherein the processing of the spent catalyst comprises raising the temperature of the spent catalyst, removing coke deposits from the spent catalyst, contacting the spent catalyst with one or more reactive gases, or combinations of these to produce a combusted catalyst;
   passing at least a portion of the combusted catalyst from the catalyst processing portion of the reactor system into a catalyst withdrawal system comprising a catalyst withdrawal vessel and a transfer line coupling the catalyst withdrawal vessel to the catalyst processing portion, each of the catalyst withdrawal vessel and the transfer line comprising an outer metallic shell and an inner refractory lining;
   cooling the combusted catalyst in the catalyst withdrawal vessel from a temperature of greater than or equal to 680° C. to a temperature of less than or equal to 350° C.; and
   withdrawing the combusted catalyst from the catalyst withdrawal vessel after the combusted catalyst has been cooled to the temperature of less than or equal to 350° C., wherein the withdrawing of the combusted catalyst from the catalyst withdrawal vessel removes the combusted catalyst from the reactor system.

2. The method of claim 1, wherein the inner refractory lining of the catalyst withdrawal vessel, the transfer line, or both is a thermal shock resistant refractory material having a coefficient of linear thermal expansion (CTE) of less than or equal to $2.7 \times 10^{-6}$ $K^{-1}$, according to ASTM E831-14.

3. The method of claim 2, wherein the thermal shock resistant refractory material comprises at least one of fused silica, vitreous silica, cordierite, or a combination of these.

4. The method of claim 1, wherein the inner refractory lining of the catalyst withdrawal vessel, the transfer line, or both is a thermal shock resistant refractory material having a strength loss of less than or equal to 25% according to the modulus of rupture standard described in ASTM C-1171.

5. The method of claim 1, wherein the catalyst withdrawal vessel is close coupled to the catalyst processing portion of the reactor system such that an outer wall of the catalyst withdrawal vessel is within 50 feet of the catalyst processing portion of the reactor system.

6. The method of claim 1, wherein at least a portion of the combusted catalyst is withdrawn from the catalyst processing portion of the reactor system into the catalyst withdrawal system batch-wise or semi-continuous during operation of the reactor system.

7. The method of claim 1, further comprising passing a fluid through the catalyst withdrawal vessel and the combusted catalyst in the catalyst withdrawal vessel.

8. The method of claim 7, wherein the fluid comprises nitrogen, argon, air, steam, or combinations thereof, and wherein the fluid has a temperature less than 350° C.

9. The method of claim 1, further comprising:
   passing the combusted catalyst removed from the catalyst withdrawal vessel to a classifier;
   classifying the combusted catalyst into a smaller particle-size catalyst and a larger particle-size catalyst, wherein the larger particle-size catalyst has an average particle size greater than the smaller particle-size catalyst;
   passing the smaller particle-size catalyst back to the reactor system;
   re-impregnating the larger particle-size catalyst with a catalytically active material to form a re-impregnated catalyst; and
   passing the re-impregnated catalyst back to the reactor system.

10. The method of claim 1, wherein the reaction comprises dehydrogenation.

11. The method of claim 1, wherein:
    processing the spent catalyst comprises contacting the spent catalyst with one or more reactive gases; and
    the one or more reactive gases comprises air.

12. The method of claim 1, wherein:
    wherein processing the spent catalyst comprises raising the temperature of the spent catalyst; and
    raising the temperature of the spent catalyst comprises combusting a supplemental fuel in the presence of the spent catalyst.

13. The method of claim 1, wherein the inner refractory lining of the catalyst withdrawal vessel, the transfer line, or both is a thermal shock resistant refractory material having a coefficient of linear thermal expansion (CTE) of less than or equal to $1.8 \times 10^{-6}$ $K^{-1}$, according to ASTM E831-14.

14. The method of claim 1, wherein the inner refractory lining of the catalyst withdrawal vessel, the transfer line, or both is a thermal shock resistant refractory material having a strength loss of less than or equal to 15% according to the modulus of rupture standard described in ASTM C-1171.

* * * * *